(12) United States Patent
Rekosh et al.

(10) Patent No.: US 7,875,604 B2
(45) Date of Patent: Jan. 25, 2011

(54) COMPOUNDS THAT INHIBIT HIV PARTICLE FORMATION

(75) Inventors: David Rekosh, Earlysville, VA (US); Marie-Louise Hammarskjöld, Earlysville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 953 days.

(21) Appl. No.: 10/588,444

(22) PCT Filed: Feb. 1, 2005

(86) PCT No.: PCT/US2005/003165

§ 371 (c)(1), (2), (4) Date: Aug. 4, 2006

(87) PCT Pub. No.: WO2005/076861

PCT Pub. Date: Aug. 25, 2005

(65) Prior Publication Data

US 2008/0318959 A1 Dec. 25, 2008

Related U.S. Application Data

(60) Provisional application No. 60/541,632, filed on Feb. 4, 2004, provisional application No. 60/569,354, filed on May 7, 2004, provisional application No. 60/574,909, filed on May 27, 2004, provisional application No. 60/583,173, filed on Jun. 25, 2004.

(51) Int. Cl.
*C07H 19/04* (2006.01)
*C07H 17/02* (2006.01)
*C07H 5/04* (2006.01)
*C07H 19/00* (2006.01)
*C07H 19/22* (2006.01)
*A61K 31/545* (2006.01)

(52) U.S. Cl. .................... 514/203; 536/17.2; 536/17.3; 536/18.7; 536/26.7; 536/17.5

(58) Field of Classification Search .................. None
See application file for complete search history.

(56) References Cited

PUBLICATIONS

Gait et al. Progress in anti-HIV structure-based drug design. Trends in Biotechnology Oct. 1995, vol. 13, No. 10, p. 430-438.*
Hendrix et al. Pharmacokinetics and Safety of AMD-3100, a Novel Antagonist of the CXCR-4 Chemokine Receptor, in Human Volunteers. Antimicrobial Agents and Chemotherapy, Jun. 2000, vol. 44, No. 6, p. 1667-1673.*
Buss et al. Measuring the effectiveness of antiretroviral agents. Antiviral Therapy 2001, vol. 6, pp. 1-7.*
Yin et al. Overcoming HIV drug resistance through rational drug design based on molecular, biochemical, and structural profiles of HIV resistance. Cellular and Molecular Life Sciences Aug. 2006, vol. 63(15), p. 1706-1724.*

(Continued)

*Primary Examiner*—Zachariah Lucas
*Assistant Examiner*—Louise Humphrey
(74) *Attorney, Agent, or Firm*—Rodney L. Sparks

(57) ABSTRACT

The present invention describes novel methods of identifying compounds which inhibit HIV particle formation and Rev-dependent HIV production. The present invention also provides methods and compounds for inhibiting HIV particle formation and or treating patients infected with HIV.

3 Claims, 18 Drawing Sheets

Code Name: 103833

Specs Name: AE-848/34435011

Chemical Name: 3-amino-5-ethyl-4,6-dimethylthieno[2,3-b]pyridine-2-carboxamide,

OTHER PUBLICATIONS

Lee et al. Toxicity of Nucleoside Analogues Used to Treat AIDS and the Selectivity of the Mitochondrial DNA Polymerase. Biochemistry 2003, vol. 42, No. 50, p. 14711-14719.*

Greene et al. Novel targets for HIV therapy. Antiviral Research 2008, vol. 80, p. 251-265.*

Olszewski et al. Guanidine alkaloid analogs as inhibitors of HIV-1 Nef interactions with p53, actin, and p56. The Proceedings from the National Academy of Science, U.S.A Sep. 2004, vol. 101, No. 39, pp. 14079-14084.*

* cited by examiner

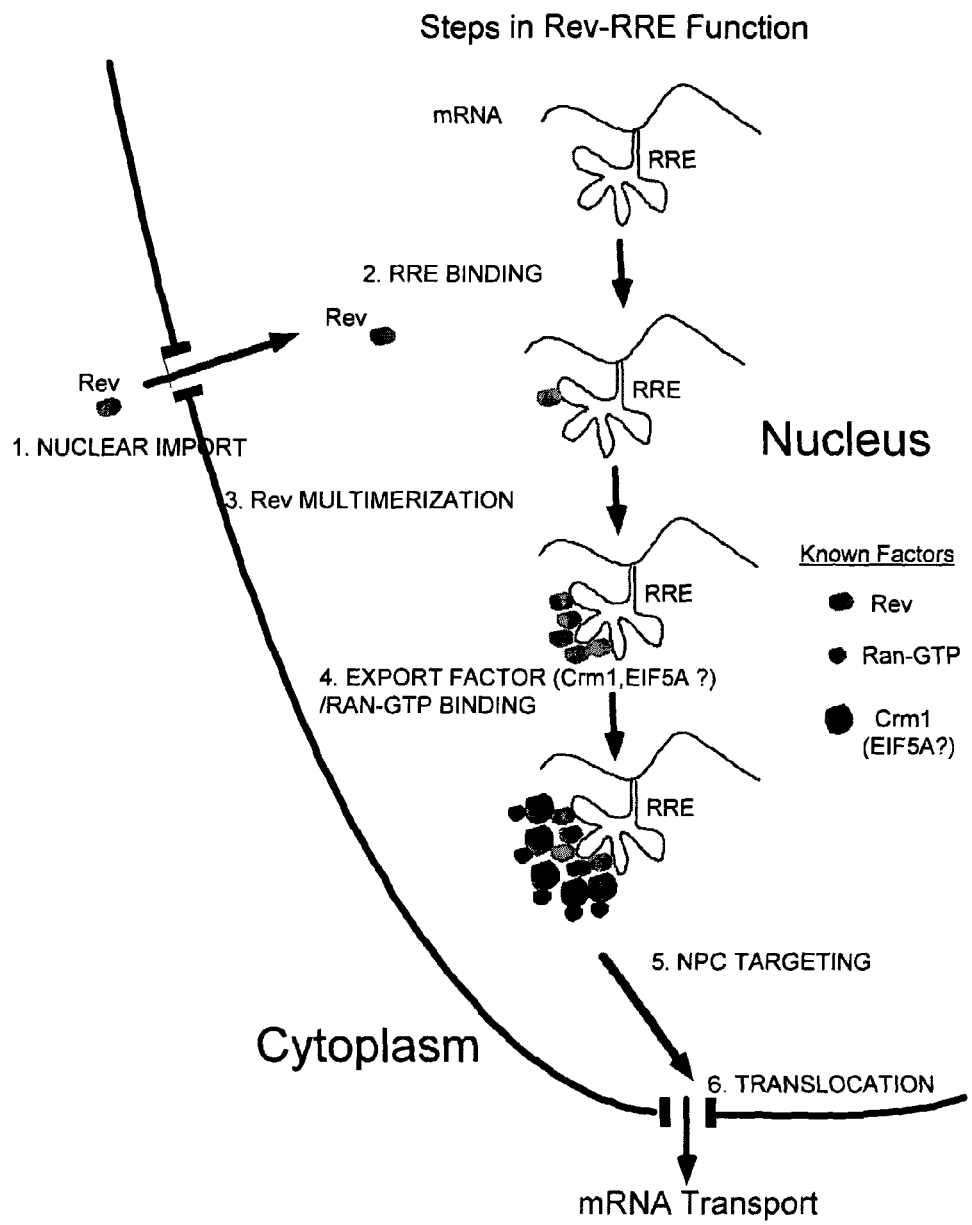
Figure 1: Known Steps in the Rev/RRE Pathway

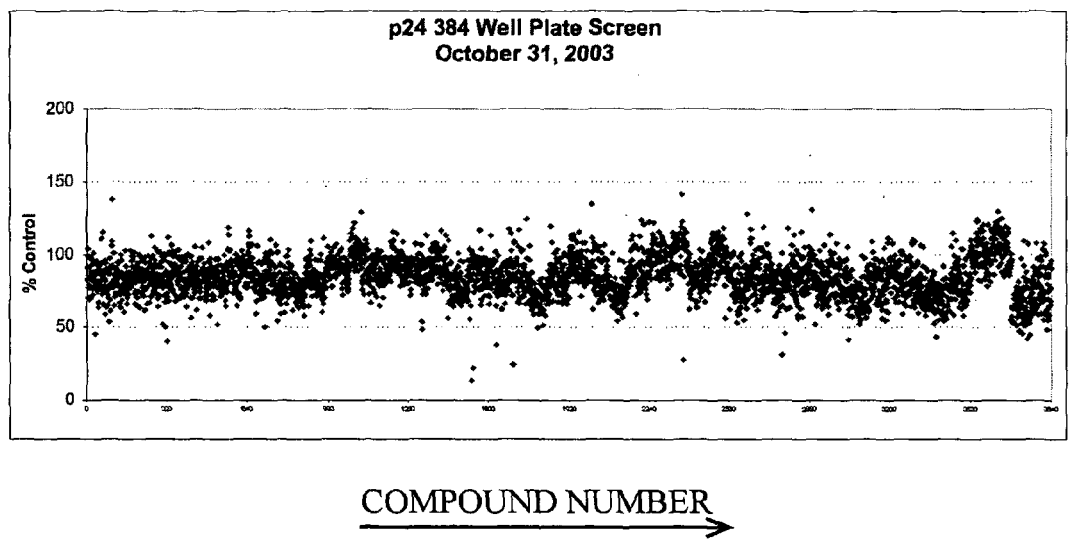
Figure 2 Screening of approximately 4000 compounds out of 40,000 total screened (9 other similar graphs not shown). Compounds that gave an inhibition of HIV particle formation below 50% were chosen for further study.

3A Dose Response (p24) and Toxicity (MT4) Assays Compound 75168
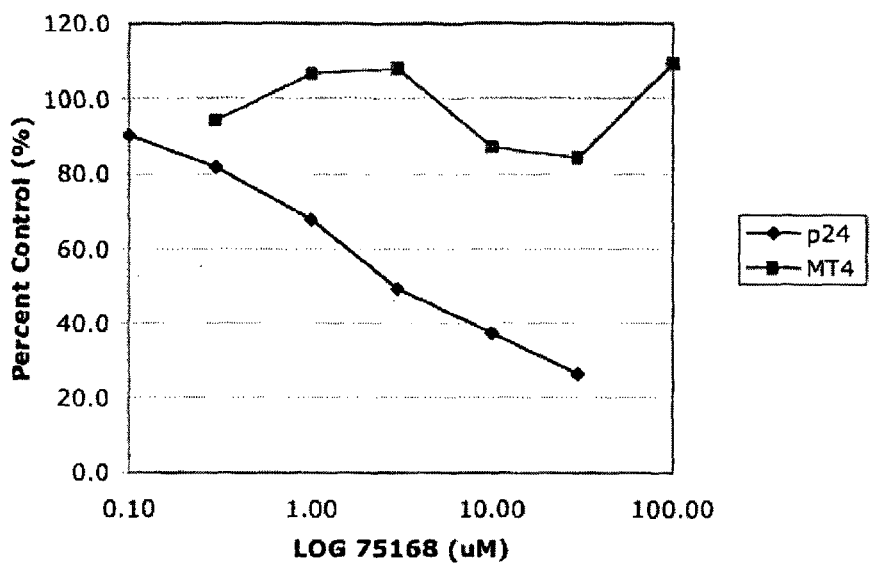
3B Dose Response (p24) and Toxicity (MT4) Assays Compound 89246
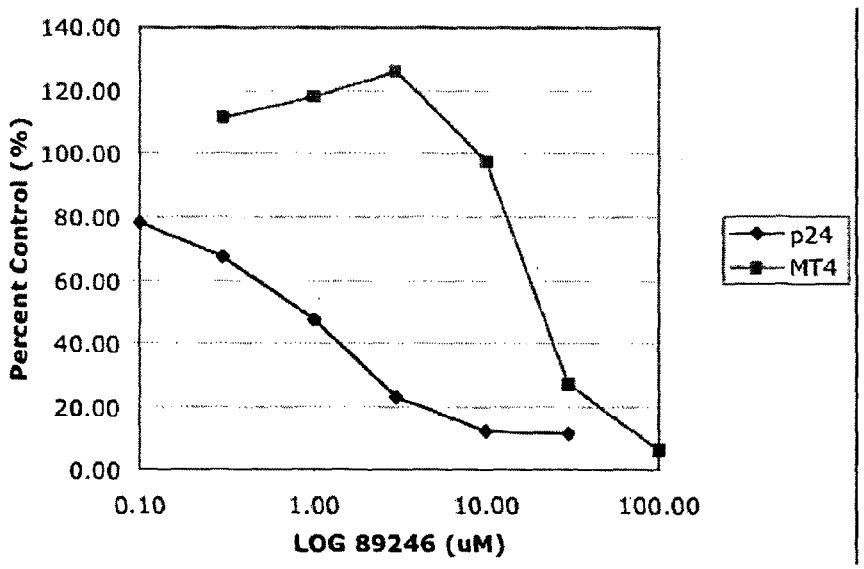
Figure 3: Six point dose response assay in 5BD.1 cells and toxicity assay in MT4 cells. This is the type of data used to calculate the $IC_{50}$ and $TC_{50}$ of each compound.

Figure 4
4A
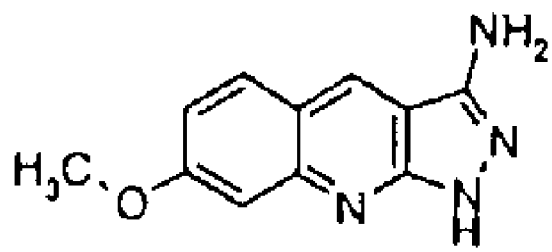
Code Name: 89246
Specs Name: AG-690/40701421
Chemical Name: 7-methoxy-1H-pyrazolo[3,4-b]quinolin-3-ylamine,
4B
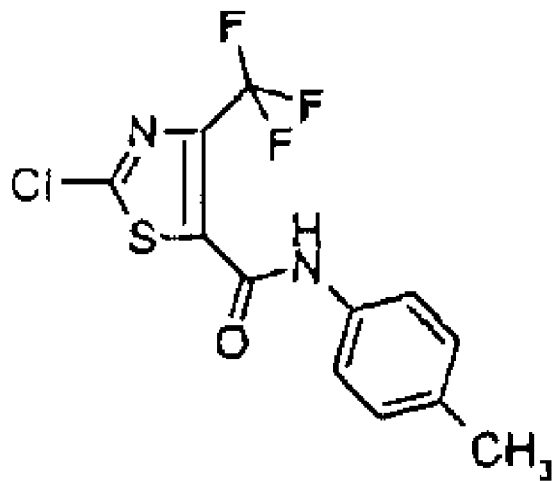
Code Name: 91161
Specs Name: AP-501/40888738
Chemical Name: 2-chloro-N-(4-methylphenyl)-4-(trifluoromethyl)-1,3-thazole-5-carboxamide,

Figure 4
4C
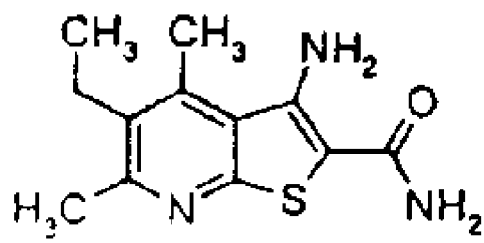
Code Name: 103833
Specs Name: AE-848/34435011
Chemical Name: 3-amino-5-ethyl-4,6-dimethylthieno[2,3-b]pyridine-2-carboxamide,
4D
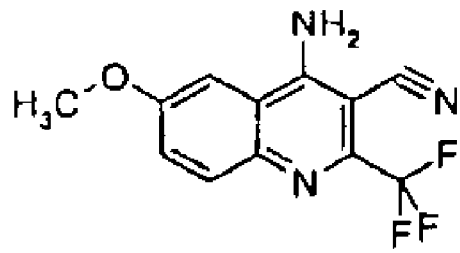
Code Name: 104366
Specs Name: AG-687/25019010
Chemical Name: 4-amino-6-methoxy-2-(trifluoromethyl)-3-quinolinecarbonitrile,

Figure 4
4E
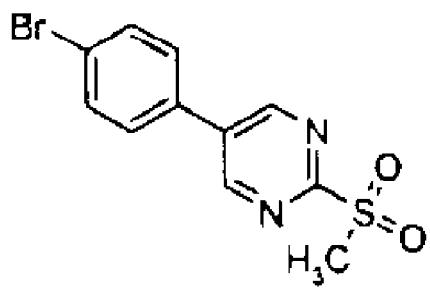
Code Name: 107129
Specs Name: AC-907/25005415
Chemical Name: -(4-bromophenyl)-2-(methylsulfonyl)pyrimidine
4F
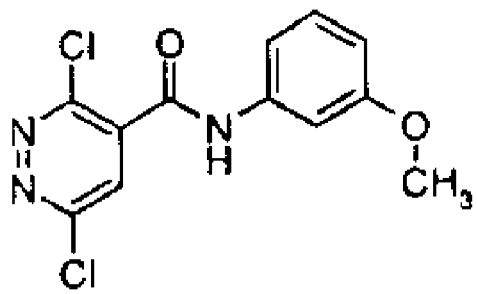
Code Name: 107740
Specs Name: AF-399/40653810
Chemical Name: 3,6-dichloro-N-(3-methoxyphenyl)-4-pyridazinecarboxamide,

Figure 4
4G
and
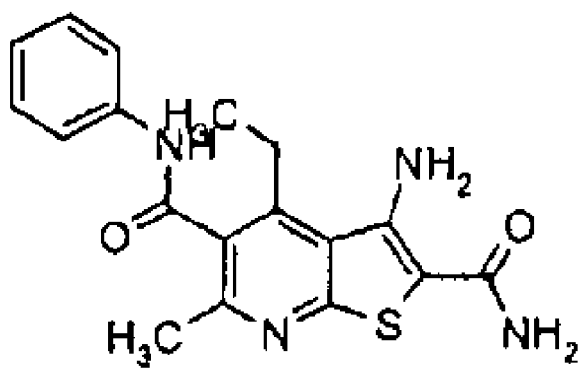
Code Name: 75168
Specs Name: AE-848/34435026
Chemical Name: 3-amino-4-ethyl-6-methyl-N~5~-phenylthieno[2,3-b]pyridine-2,5-dicarboxamide,
4H
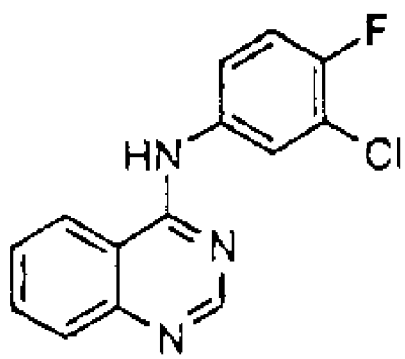
Code Name: 109020
Specs Name: AP-906/41641102
Chemical Name: N-(3-chloro-4-fluorophenyl)-N-(4-quinazolinyl)amine

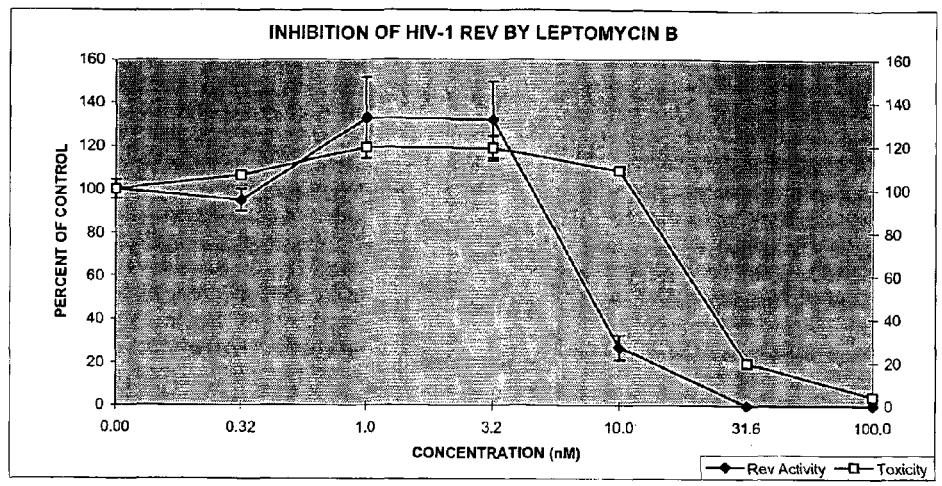
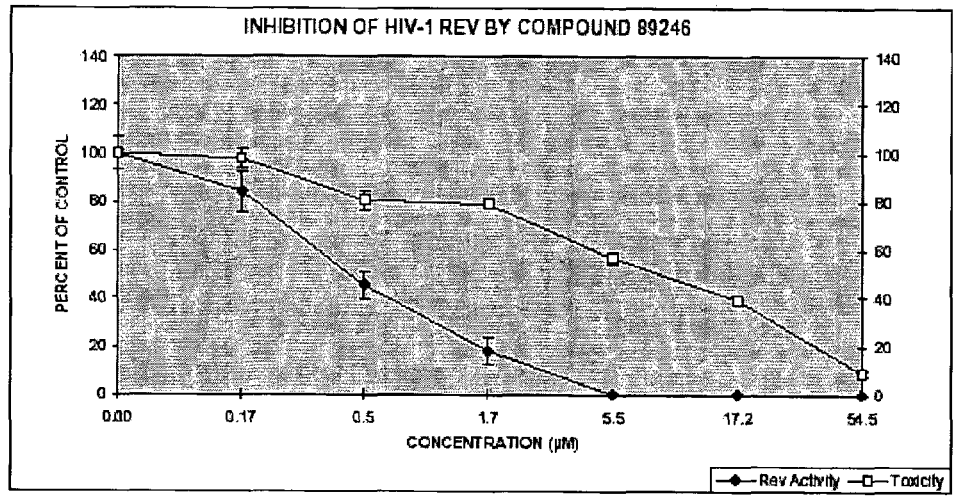
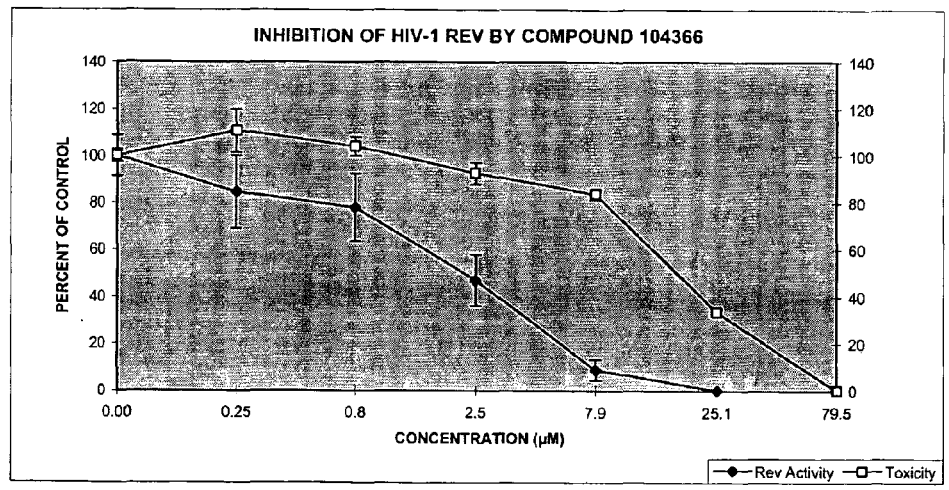
Figure 5

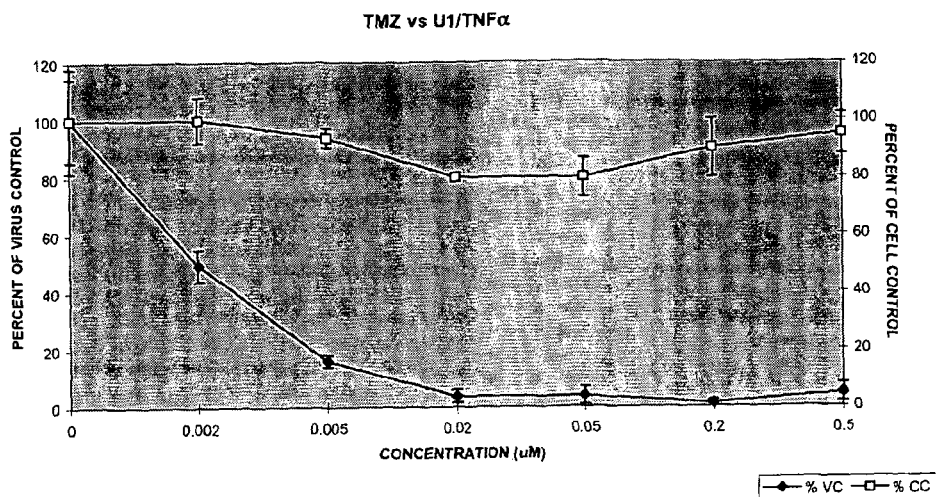
8A
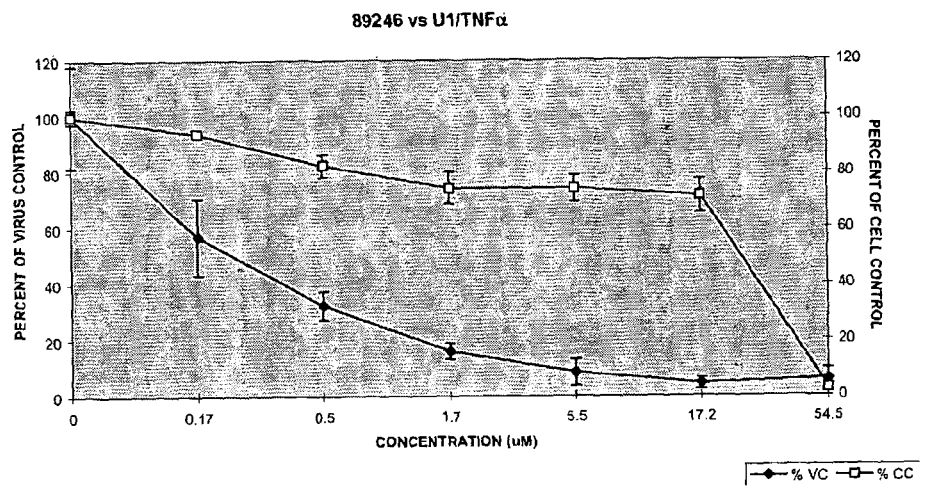
8B
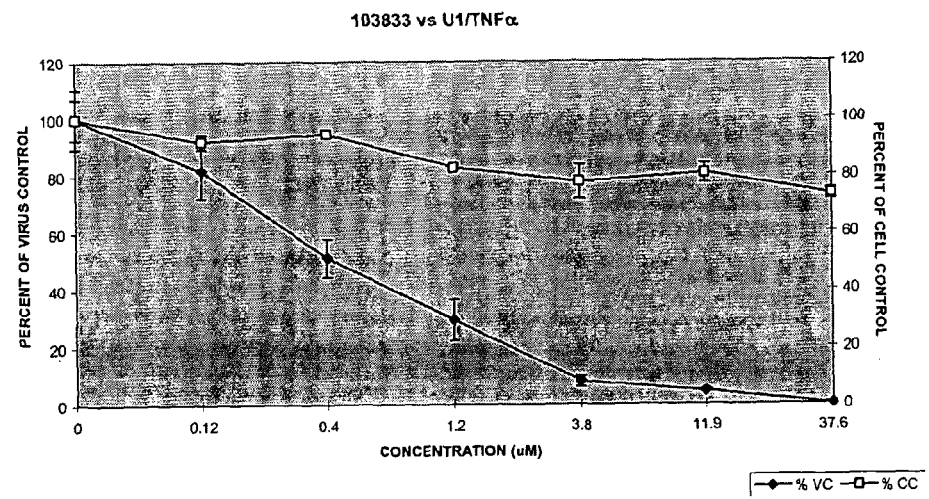
8C
Figure 8

Figure 9
Analogs of 89246
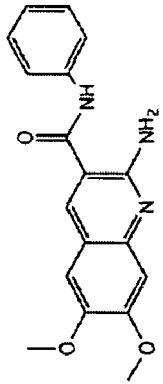
Specs name: AG-205/40649270  Code name: 113
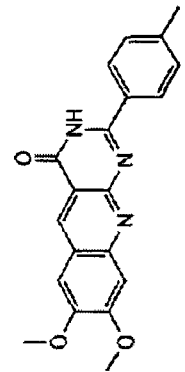
Specs name: AG-205/41004335  Code name: 114
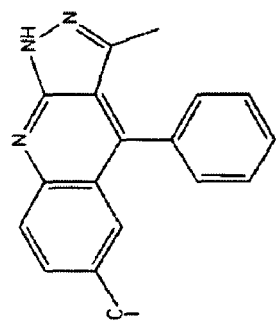
Specs name: AH-034/34961017  Code name: 111
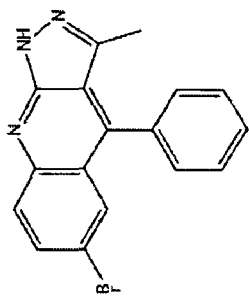
Specs name: AH-283/08743005  Code name: 112
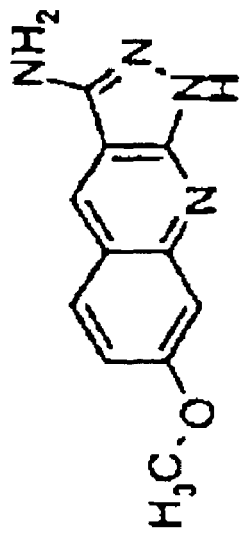
Code Name: 89246
Specs Name: AG-690/40701421
PARENTAL COMPOUND

Figure 10
Analogs of 91161

| Specs name: AP-501/40804729 | Code: 411 |
| Specs name: AP-501/40804731 | Code: 412 |
| Specs name: AP-501/40804735 | Code: 413 |
| Specs name: AP-501/40804576 | Code: 414 |

| Specs name: AP-501/40804757 | Code: 415 |
| Specs name: AP-501/40888735 | Code: 416 |
| Specs name: AP-501/40888736 | Code: 417 |
| Specs name: AP-501/40888737 | Code: 418 |

| Specs name: AP-501/42581233 | Code: 419 |
| Specs name: AP-501/42583410 | Code: 420 |
| Specs name: AP-501/42861930 | Code: 421 |
| Specs name: AP-501/42861933 | Code: 422 |
| Specs name: AP-501/42861938 | Code: 423 |

Code Name: 91161
Specs Name: AP-501/40888738
PARENTAL COMPOUND

Analogs of 103833

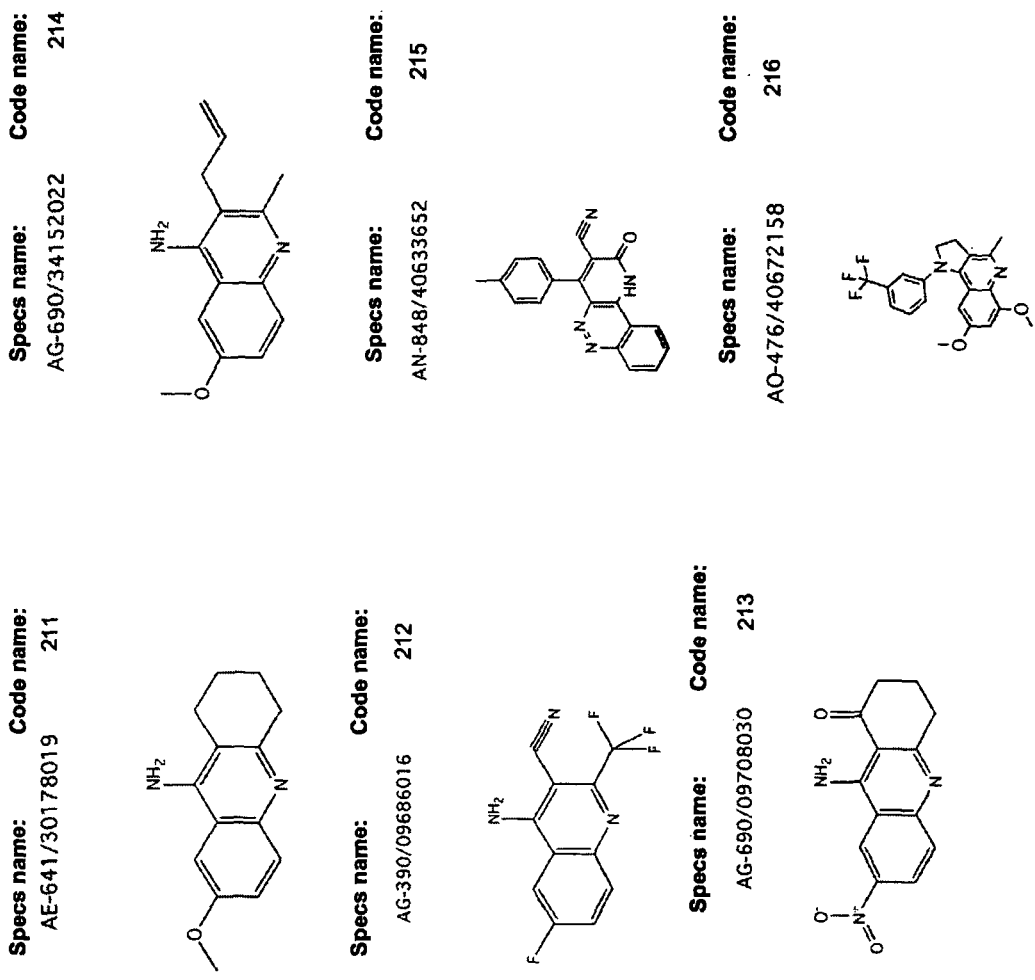
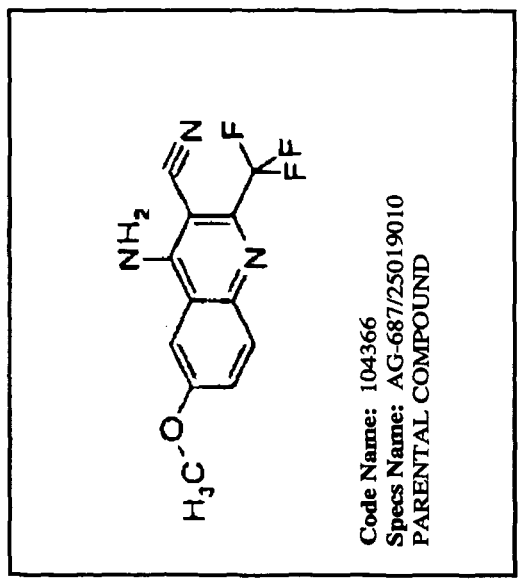
Figure 12
Analogs of 104366

Analogs of 107129

Specs name: AF-399/40653844  Code: 514
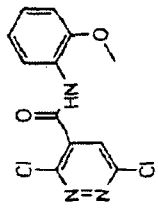
Specs name: AF-399/40653847  Code: 515
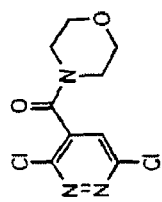
Specs name: AM-944/40947865  Code: 516
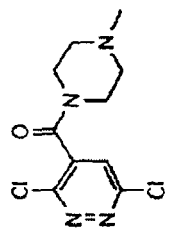
Specs name: AF-399/40653811  Code: 511
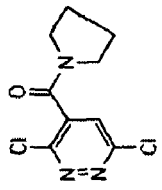
Specs name: AF-399/40653841  Code: 512
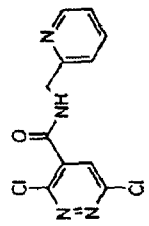
Specs name: AF-399/40653842  Code: 513
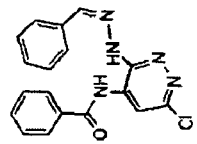
Figure 14
Analogs of 107740
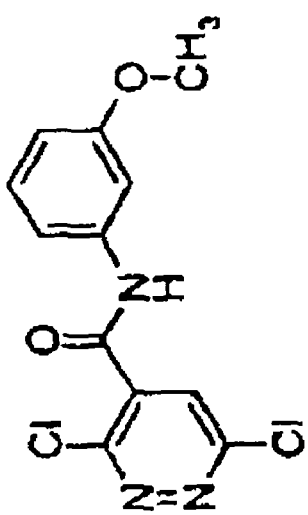
Code Name: 107740
Specs Name: AF-399/40653810
PARENTAL COMPOUND Analogs of 109020

COMPOUNDS THAT INHIBIT HIV PARTICLE FORMATION

CROSS REFERENCE TO RELATED APPLICATIONS

This application is a national stage filing of International Application No. PCT/US2005/003165, filed on Feb. 1, 2005, which is entitled to priority pursuant to 35 U.S.C. §119(e) to U.S. provisional patent application nos. 60/541,632, filed Feb. 4, 2004, 60/569,354, filed May 7, 2004, 60/574,909, filed May 27, 2004, and 60/583,173, filed Jun. 25, 2004, the entire disclosures of which are hereby incorporated by reference herein in their entirety.

US GOVERNMENT RIGHTS

This invention was made with United States Government support under Grant Nos. R21 AI54213-01, and R21 AI54213-02, awarded by National Institutes of Health. The United States Government has certain rights in the invention.

BACKGROUND

The Rev protein is absolutely essential for the production of the viral structural proteins and thus inhibition of Rev function leads to inhibition of HIV replication through prevention of structural protein synthesis and the assembly of HIV particles (For a review on Rev see Pollard, V. W., and M. H. Malim. 1998. Annu Rev Microbiol. 52:491-532). This is most easily shown using proviral clones that lack a functional rev gene, in that they have no replicative ability (Feinberg et al 1986 Cell 46:807-817; Bray et al. 1994 PNAS 91:1256-60). In the absence of functional Rev, genomic HIV RNA and several other HIV mRNAs remain in the cell nucleus (Felber et al. 1989 Proc Natl Acad Sci USA. 86:1496-1499; Hammarskjold et al. 1989, J Virol. 63:1959-1966; Malim et al. Nature. 338:254-257). Since the RNA is not exported to the cytoplasm, viral structural proteins are not made and the infectious cycle cannot continue. Thus, it is clear that modalities inhibiting the function of Rev can form the basis for therapy against HIV infection and AIDS.

Although the Rev/RRE export pathway is still not fully understood, several important steps in this pathway have now been identified. The current understanding of this process is schematically shown in FIG. 1. The pathway starts with the import of Rev into the nucleus (step 1). In step 2, Rev binds specifically to RNA containing a specific RNA element called the Rev Response Element (RRE). In step 3, Rev multimerizes on the RRE in a process believed to involve protein-protein as well as protein-RNA interactions. In step 4, the Rev-RRE complex is recognized by CRM1 and RAN-GTP, which initiates the export process and eventually targets the complex to the nuclear pore (Step 5), where it interacts with nucleoporins resulting in translocation to the cytoplasmic side of this complex (Step 6). Many details in the pathway have yet to be elucidated. Other soluble cellular proteins (e.g. EIF5A) may also play a specific role in the Rev/RRE pathway. It is also not clear what happens once the complex reaches the cytoplasm.

Viral replication inhibited by attacking required steps of Rev function described above has been demonstrated through the use of different classes of Rev mutants (Berger et al. 1991 Virology. 183:630-635). Mutants in each of the Rev functional domains have been described which abolish viral replication. Additionally, a dominant negative form of the Rev protein has been used to inhibit viral replication (Malim et al. 1992. J Exp Med. 176:1197-1201).

The HIV virus particle consists of internal proteins that make up the viral core and two proteins that are part of the lipid envelope that surrounds the core. These proteins are expressed from precursor molecules called Pr55gag and Pr160gagpol for the core proteins and gp160 for the envelope proteins. It is known that expression of these proteins normally requires co-expression of the HIV Rev protein. Without the Rev protein, the mRNAs encoding each of these proteins remains in the nucleus. In order for the Rev protein to work, it is also essential to have an element present in the RNA that binds to Rev. This element is called the RRE.

There is a long felt need in the art for a better method to identify compounds capable of inhibiting HIV replication and Rev function. The present invention satisfies these needs.

SUMMARY OF THE INVENTION

The present invention is directed to novel methods of identifying HIV inhibitory compounds and the use of those compounds to treat patients that are HIV positive. The present invention is also directed to a safe quantitative in vitro high-throughput assay to screen library compounds for effects on Rev-dependent p24 production. In one aspect, the methods of the invention are directed to identifying inhibitors of HIV replication.

There is clear evidence that Human Immunodeficiency Virus (HIV) is the cause of AIDS and that drugs that inhibit the replication and production of infectious HIV particles are efficacious in the treatment of AIDS. This disclosure describes the identification of many compounds which are very effective inhibitors of HIV particle formation. Without wishing to be bound by any particular theory, the compounds may act by inhibiting HIV Rev function, HIV assembly, HIV particle budding or some other part of the HIV life cycle. The compounds are therefore likely to form the chemical basis for new drugs that could be used for the treatment of AIDS.

The inhibitory compounds of the present invention were identified using the 5BD.1 cell line to screen for drugs that inhibit HIV particle formation without showing toxicity in a 5 day cell survival assay. The amount of HIV particles released by budding from the 5BD.1 cell line into the culture medium was measured using a simple and straightforward ELISA assay. 40,000 compounds were screened and 12 were selected as "hits" based on their ability to inhibit HIV particle formation without showing toxicity in a 5 day cell survival assay.

Various aspects and embodiments of the invention are described in further detail below.

BRIEF DESCRIPTION OF THE DRAWINGS

FIG. 1 schematically illustrates known steps in the Rev/RRE pathway.

FIG. 2 graphically summarizes the ELISA data readout from part of the primary screen of 40,000 compounds plotted as a percentage of the control. Compounds that gave an inhibition of HIV particle formation below 50% were chosen for further study. In the total screen, 192 compounds gave values below 50%.

FIG. 3 is a graphic illustration of a dose response curve testing the compounds 75168 (upper panel) and 89246 (lower panel) for effects on HIV particle release from cell lines and on toxicity. The data illustrate a six concentration dose response experiment for the compounds added to the cell line and are indicate measurement of p24 (diamonds) in 5BD.1 cells and toxicity in MT4 cells (squares). Each compound is named with an identifier along the X-axis of the graph, as are the concentrations of the compound tested. The left Y-axis indicates HIV particle release into the medium as a percentage of the control (untreated). The right Y-axis indicates toxicity as a percentage of control (untreated) and a value of 100% indicates no toxicity. into the medium as a percentage of the control (untreated). Details of the assay are given in part E.

FIG. 4, comprising FIGS. 4A to 4H, provides the chemical structures and code name, Specs name, and chemical name of eight of the compounds identified in the assays of the invention, namely: 89246 (4A), 91161 (4B), 103833 (4C), 104366 (4D), 107129 (4E), 107740 (4F), 75168 (4G), and 109020 (4H).

FIG. 5, comprising FIGS. 5A to 5C, is a graphic illustration of the results of testing leptomycin B (control; upper panel; 5A), compound 99246 (middle panel; 5B) and compound 104355 (lower panel; 5C) for inhibition of HIV-1 Rev (left ordinate) and for toxicity (right ordinate) using 5BD.1 cells. The concentration (μM) is indicated on the abscissa. Similar data were obtained for all the compounds depicted in FIG. 4 and were used to calculate $IC_{50}$ and $TC_{50}$.

Figure 6:
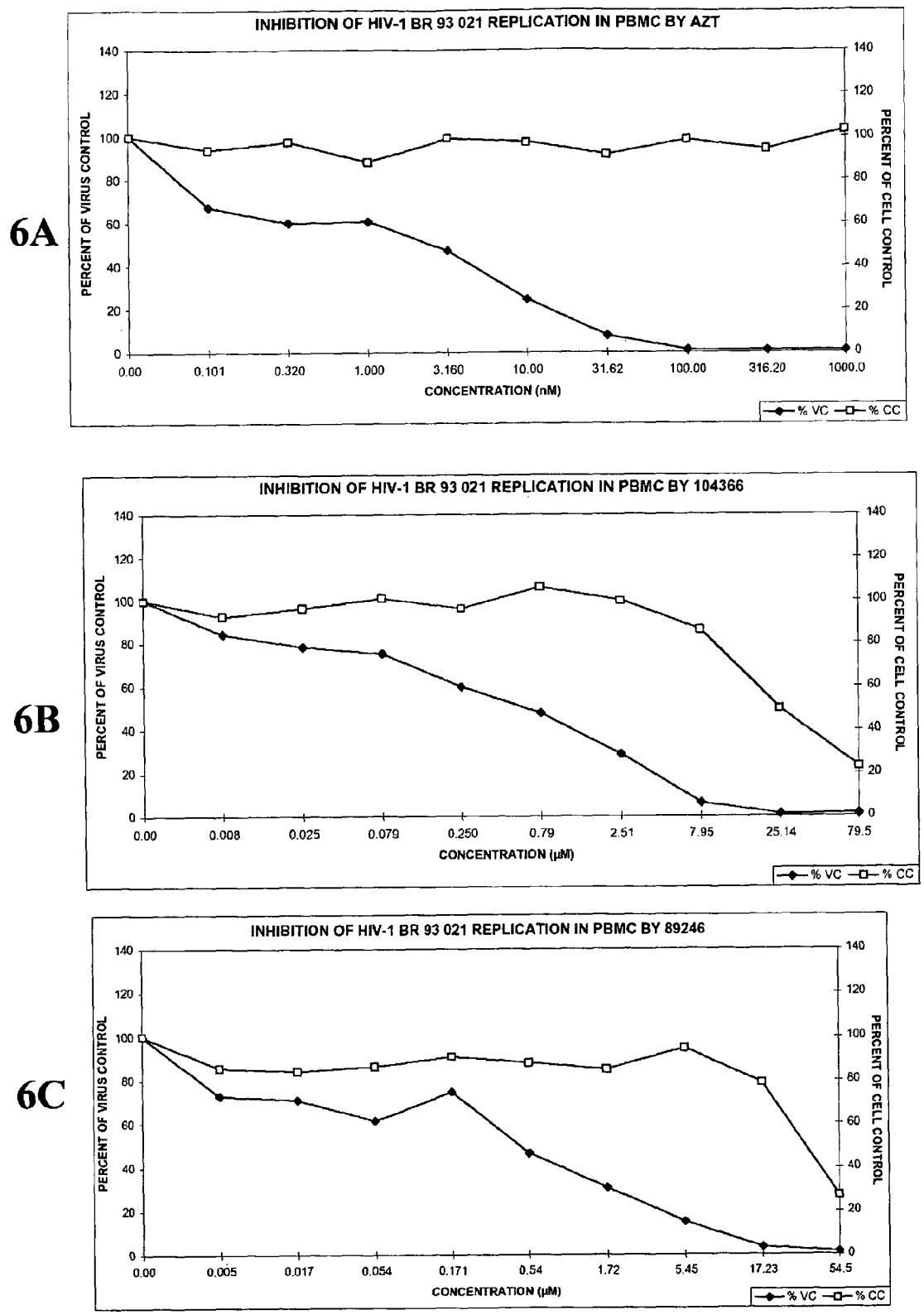

FIG. 6, comprising FIGS. 6A to 6C, is a graphic illustration of a dose response curve indicating the effects of AZT (upper panel; 6A), compound 104366 (middle panel; 6B), and compound 89246 (lower panel; 6C) in a PBMC viral replication assay with the primary isolate HIV-1 BR 93 021 (closed diamonds). Toxicity data is also plotted (open squares). Similar data for all eight compounds was used to calculate the $IC_{50}$ and $TC_{50}$.

Figure 7:
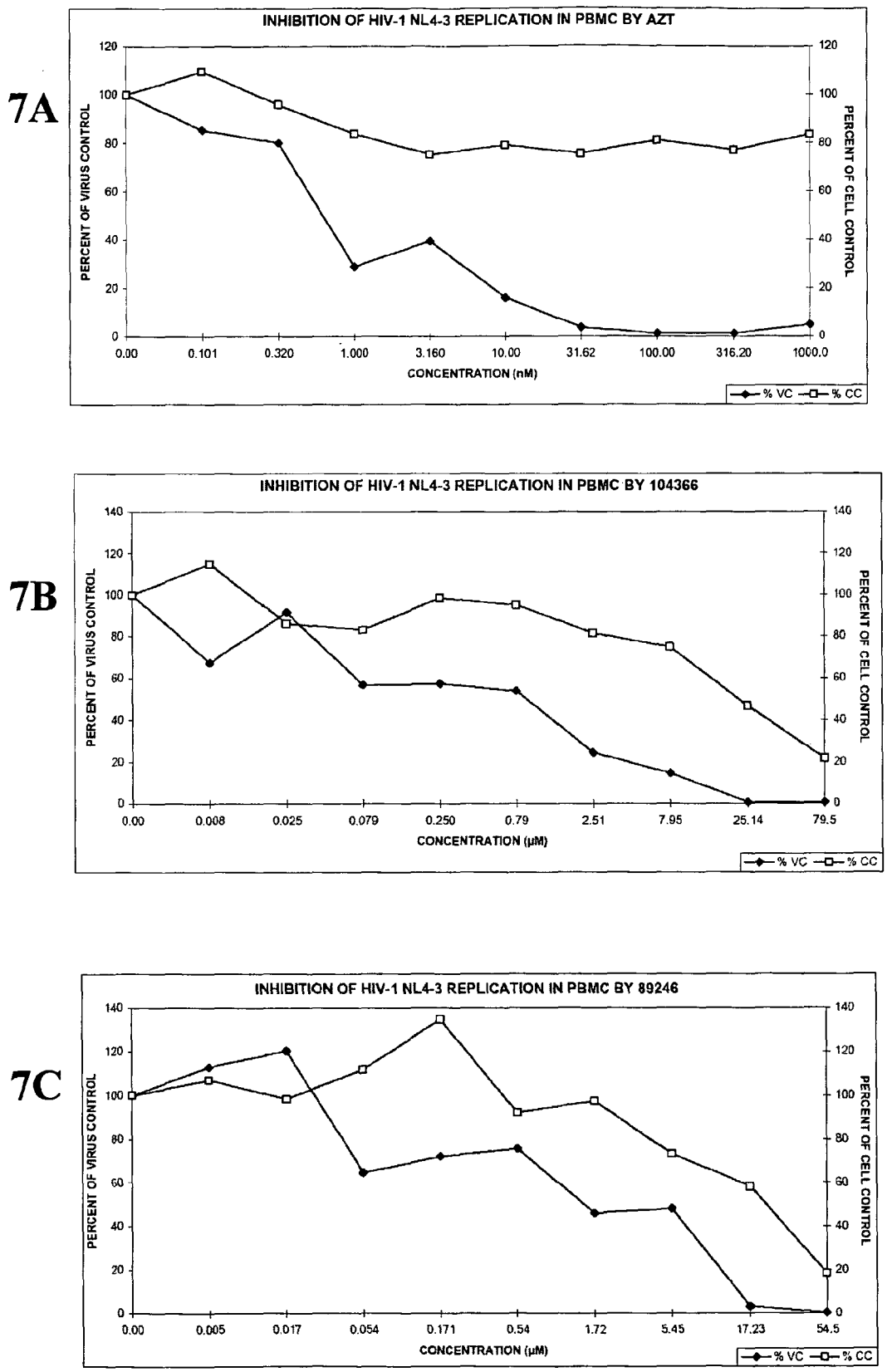

FIG. 7, comprising FIGS. 7A to 7C, graphically illustrates the response to the AZT control (upper panel; 7A), compound 104366 (middle panel; 7B), and compound 89246 (lower panel; 7C) with the lab isolate HIV-1 NL4-3 (diamonds) in a PBMC viral replication assay. Toxicity data is also plotted (squares). Similar data for all eight compounds was used to calculate the $IC_{50}$ and $TC_{50}$. VC=viral control (diamonds); CC=cell control (squares)

FIG. 8, comprising FIGS. 8A to 8C, graphically illustrates the dose response to the Temacrazine (TMZ) control (upper panel; 8A), compound 89246 (middle panel; 8B), and compound 103833 (lower panel; 8C) in a U1 latency activation assay (diamonds) and in a toxicity assay (squares). Concentration (μM) is indicated on the abscissa. Similar data for seven compounds was obtained and used to calculate the $IC_{50}$ and $TC_{50}$. Ordinates represent percent of virus control (VC; left ordinate) and percent of cell control (CC; right ordinate).

FIG. 9 schematically illustrates the structures of compound 89246 and four of its analogs.

FIG. 10 schematically illustrates the structures of compound 91161 and thirteen of its analogs.

Figure 11:
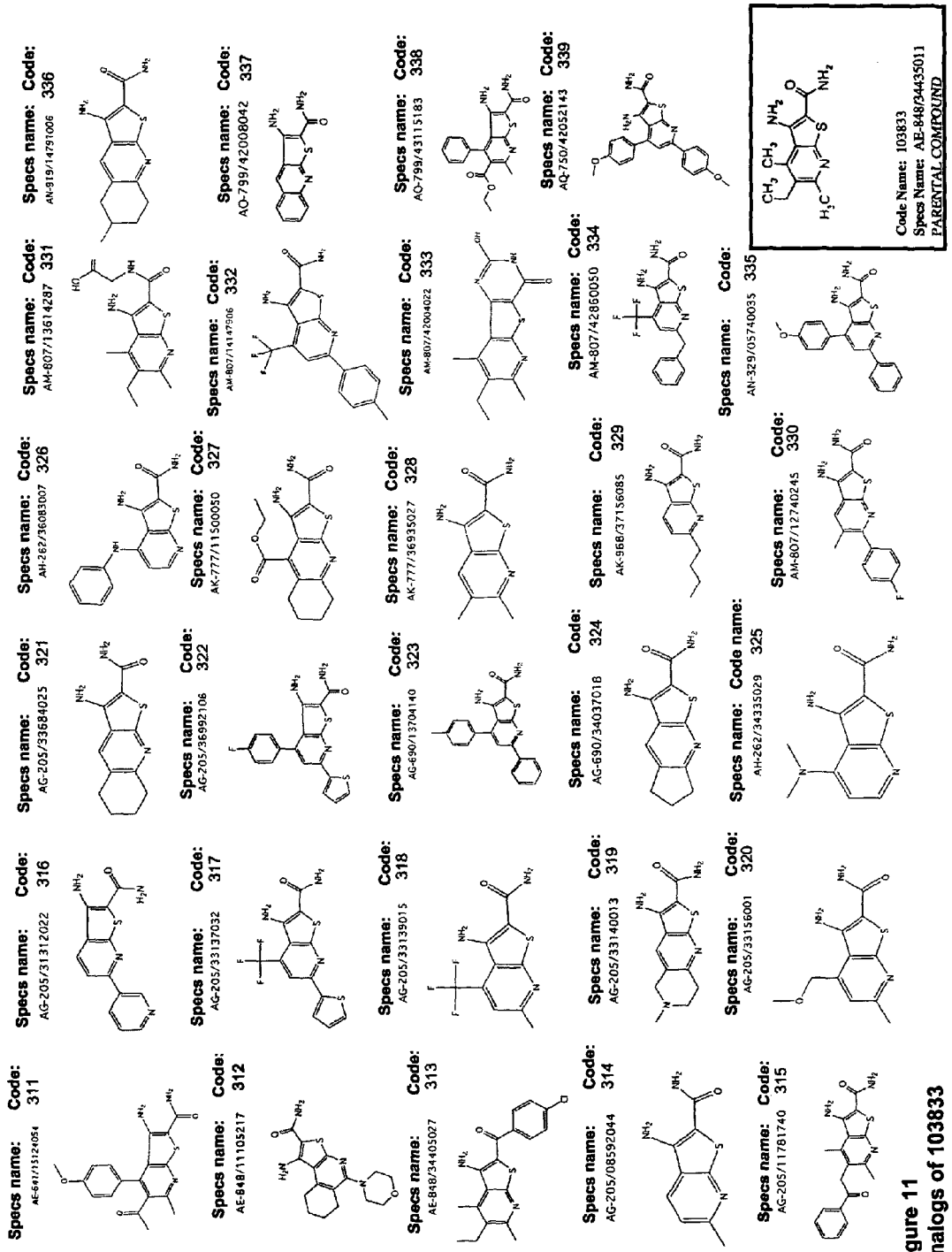

FIG. 11 schematically illustrates the structures of compound 103833 and 29 of its analogs.

FIG. 12 schematically illustrates the structures of compound 104366 and six of its analogs.

Figure 13:
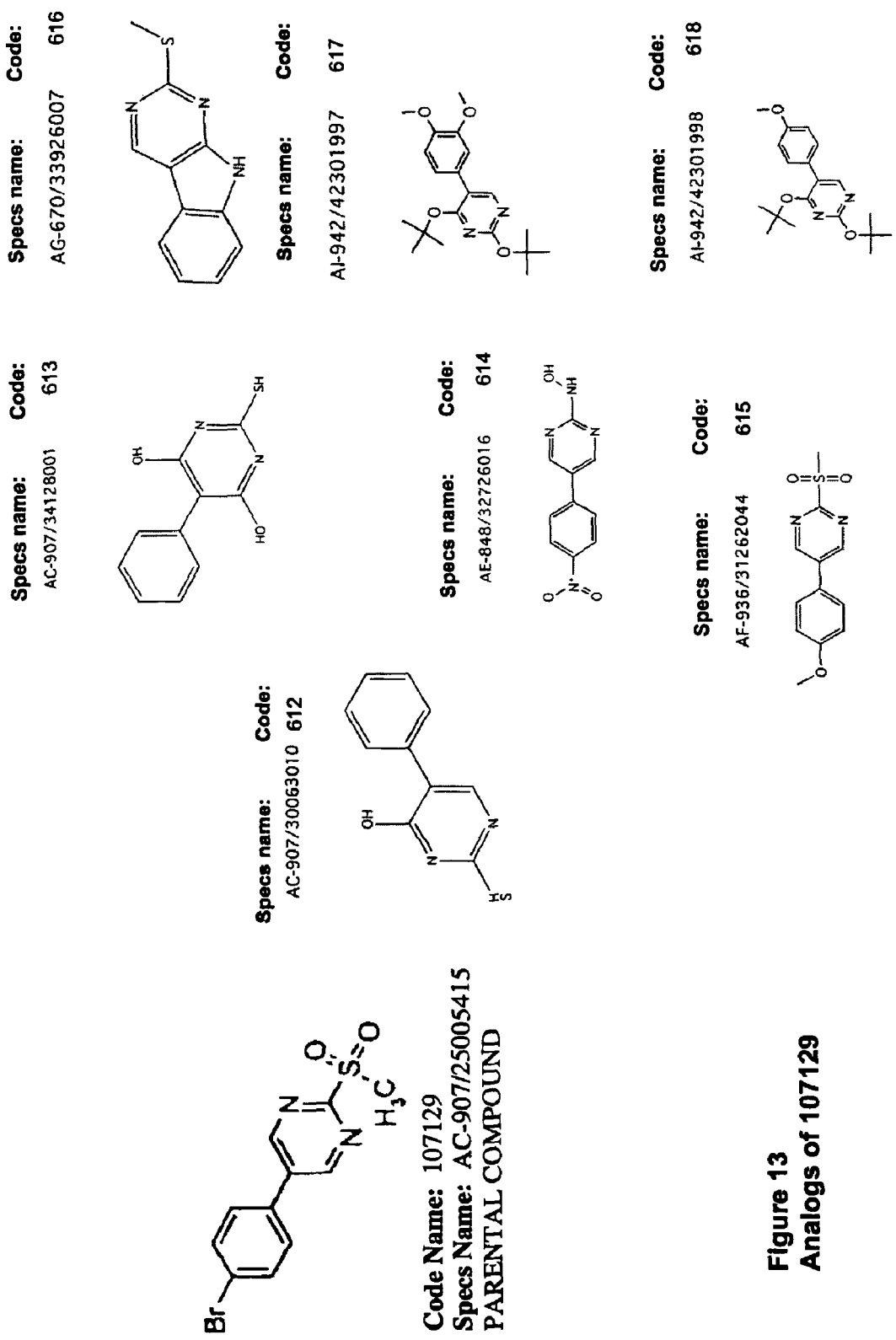

FIG. 13 schematically illustrates the structures of compound 107129 and six of its analogs.

FIG. 14 schematically illustrates the structures of compound 107440 and six of its analogs.

Figure 15:
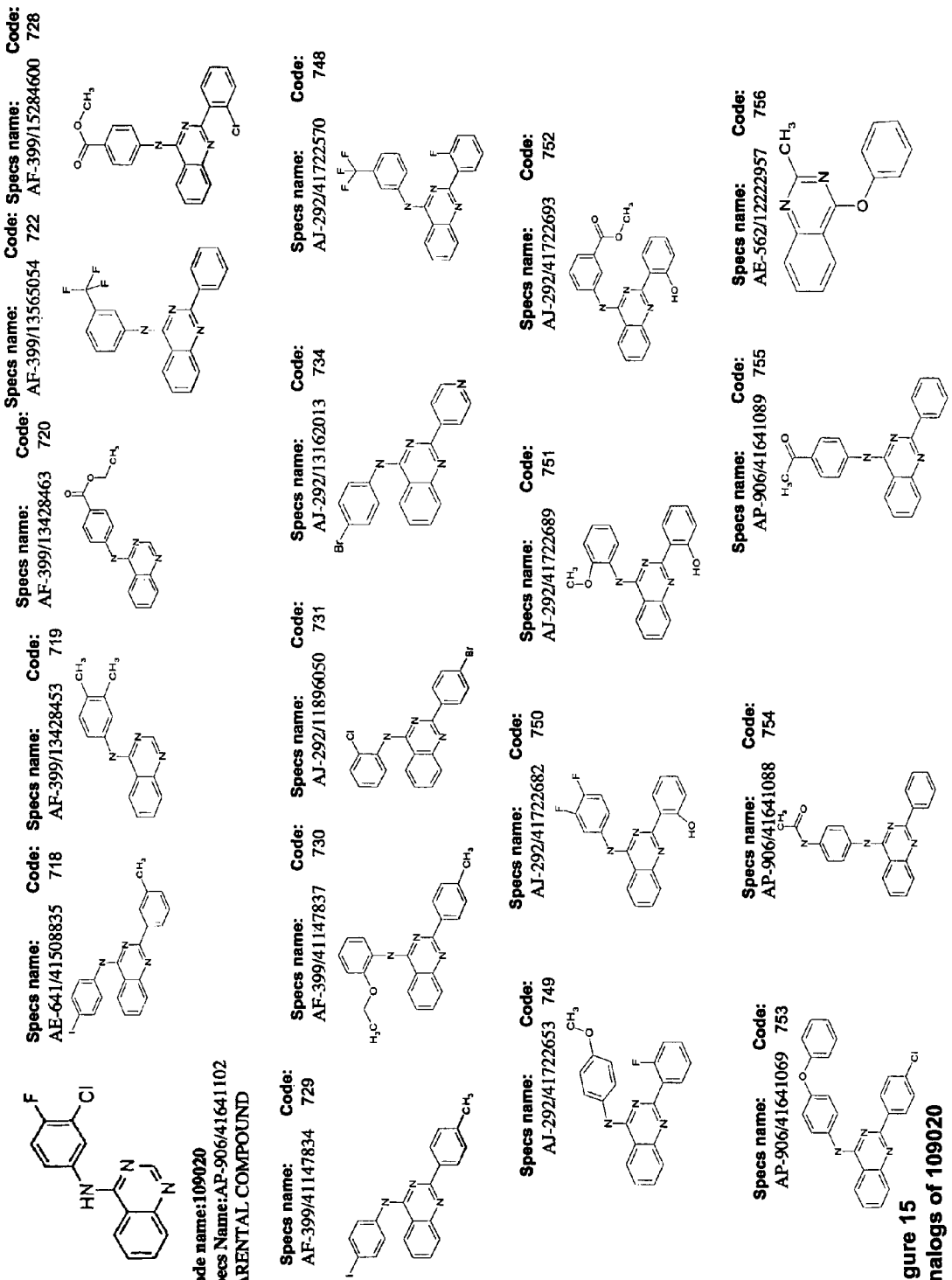

FIG. 15 schematically illustrates the structures of compound 109020 and eighteen of its analogs.

DETAILED DESCRIPTION OF THE INVENTION

Definitions

In describing and claiming the invention, the following terminology will be used in accordance with the definitions set forth below.

As used herein, the articles "a" and "an" refer to one or to more than one, i.e., to at least one, of the grammatical object of the article. By way of example, "an element" means one element or more than one element.

As used herein, an "analog" of a chemical compound is a compound that, by way of example, resembles another in structure but is not necessarily an isomer (e.g., 5-fluorouracil is an analog of thymine).

A disease or disorder is "alleviated" if the severity of a symptom of the disease or disorder, the frequency with which such a symptom is experienced by a patient, or both, are reduced.

As used herein, a "derivative" of a compound refers to a chemical compound that may be produced from another compound of similar structure in one or more steps, as in replacement of H by an alkyl, acyl, or amino group.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Inhibiting HIV replication" as used herein, refers to any method or technique which inhibits HIV particle formation, virion production, release, as well as methods the induction of such processes. The term includes inhibiting Rev expression, function, or activity.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "subject" of diagnosis or treatment is a mammal, including a human.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like.

The term ($C_5$-$C_8$ alkyl)aryl refers to any aryl group which is attached to the parent moiety via the alkyl group.

The term "heterocyclic group" refers to a mono- or bicyclic carbocyclic ring system containing from one to three heteroatoms wherein the heteroatoms are selected from the group consisting of oxygen, sulfur, and nitrogen.

As used herein the term "heteroaryl" refers to a mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "pharmaceutically-acceptable salt" refers to salts which retain the biological effectiveness and properties of the S1P analogs of the present invention and which are not biologically or otherwise undesirable. In many cases, the SIP analogs of the present invention are capable of forming acid and/or base salts by virtue of the presence of amino and/or carboxyl groups or groups similar thereto.

Embodiments

In one embodiment, the present invention is directed to a method of identifying compounds, and their analogs and derivatives, which inhibit HIV replication. HIV replication and HIV particle formation are used synonymously herein. In one aspect, the invention is directed to a method of identifying compounds with anti-rev activity. In one aspect, the invention is useful for screening many known compounds. In another aspect, the invention is useful for identifying activity of unknown compounds in mixtures such as cell or plant extracts.

In one aspect, the invention describes compounds, and analogs and derivatives thereof, which inhibit HIV particle formation by inhibiting Rev function or activity. One of ordinary skill in the art would understand that there are many methods to measure Rev function or activity. Methods and techniques for measuring Rev function and activity are useful for determining whether a compound inhibits HIV replication. Those methods not described herein are known in the art and are available to those of ordinary skill in the art. The assays described herein are useful for identifying inhibitors of HIV replication, whether the assay measures replication directly or indirectly.

In one aspect of the invention, a cell which produces HIV virions in a Rev-protein dependent fashion is contacted with a test compound. Inhibition of HIV replication in said cells, relative to HIV replication in cells treated with the test compound which produce HIV virions in a Rev-independent fashion, is a an indication that said compound inhibits Rev-dependent HIV virion production. In one aspect of the invention, cell lines useful for identifying inhibitors of HIV replication include, but are not limited to, 5BD.1, 5BA.1, and 2A.22.

In accordance with one embodiment an HIV inhibitor is provided wherein the compound has the general structure:

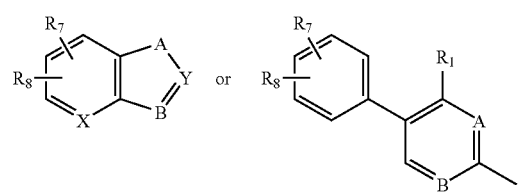

wherein

A is selected from the group consisting of N, $CR_1$, and

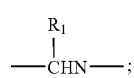

B is selected from the group consisting of N and S;

Y is selected from the group consisting of Se, CH and $CR_4$;

X is selected from the group consisting of CH and N;

R$_1$ is selected from the group consisting of H, NR$_5$R$_6$ and

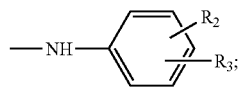

R$_2$ and R$_3$ are independently selected from the group consisting of H, halo, hydroxy and C$_1$-C$_4$ alkyl;

R$_4$ is selected from the group consisting of H, halo, hydroxy and C$_1$-C$_4$ alkyl;

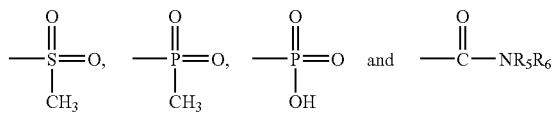

R$_5$ and R$_6$ are independently selected from the group consisting of H and C$_1$-C$_4$ alkyl;

R$_7$ and R$_8$ are independently selected from the group consisting of H, halo, hydroxy, C$_1$-C$_4$ alkyl, C$_1$-C$_4$ alkoxy, —NHC(O)CH$_3$ and —O(C$_1$-C$_4$ alkyl)(C$_5$-C$_6$ heterocyclic) or R$_7$ and R$_8$ together with the atoms to which they are attached form an optionally substituted C$_5$-C$_6$ aryl, wherein the aryl ring is optionally substituted with halo, C$_1$-C$_4$ alkyl, C$_1$-C$_4$ alkoxy, C$_1$-C$_4$ alkyl(C$_5$-C$_6$ aryl) and —O(C$_1$-C$_4$ alkyl)(C$_5$-C$_6$ heterocyclic). In one embodiment Y is CR$_4$, R$_7$ is H or C$_1$-C$_4$ alkoxy, R$_8$ is halo or

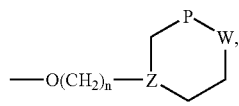

wherein n is an integer ranging from 1-5, and P, W and Z are independently selected from the group consisting of O, S, CH$_2$ and NH.

In another embodiment a compound is provided wherein the compound has the general structure:

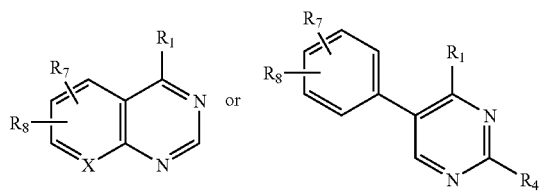

wherein

X is selected from the group consisting of CH and N;

R$_1$ is selected from the group consisting of H, NR$_5$R$_6$ and

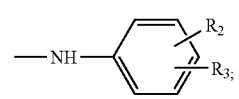

R$_2$ and R$_3$ are independently selected from the group consisting of H, halo, hydroxy and C$_1$-C$_4$ alkyl;

R$_4$ is selected from the group consisting of H, halo, hydroxy and C$_1$-C$_4$ alkyl,

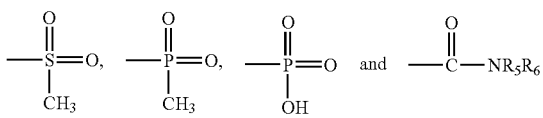

R$_5$ and R$_6$ are independently selected from the group consisting of H and C$_1$-C$_4$ alkyl;

R$_7$ and R$_8$ are independently selected from the group consisting of H, halo, hydroxy, C$_1$-C$_4$ alkyl, C$_1$-C$_4$ alkoxy, —NHC(O)CH$_3$ and —O(C$_1$-C$_4$ alkyl)(C$_5$-C$_6$ heterocyclic) or R$_7$ and R$_8$ together with the atoms to which they are attached form an optionally substituted C$_5$-C$_6$ aryl, wherein the aryl ring is optionally substituted with halo, C$_1$-C$_4$ alkyl, C$_1$-C$_4$ alkoxy, C$_1$-C$_4$ alkyl(C$_5$-C$_6$ aryl) and —O(C$_1$-C$_4$ alkyl)(C$_5$-C$_6$ heterocyclic). In one embodiment R$_1$ is NR$_5$R$_6$ or

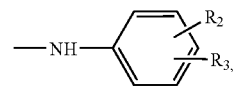

R$_7$ is H or C$_1$-C$_4$ alkoxy, and

R$_8$ is halo or

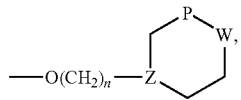

wherein n is an integer ranging from 1-5, and P, W and Z are independently selected from the group consisting of O, S, CH$_2$ and NH.

Another embodiment of the invention is directed to compounds of the invention identified as inhibitors of Rev-activity, such as the following eight compounds, as well as analogs, modifications, and derivatives thereof:

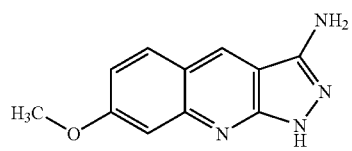

Code Name: 89246
Specs Name: AG-690/40701421
Chemical Name: 7-methoxy-1H-pyrazolo[3,4-b]quinolin-3-ylamine,

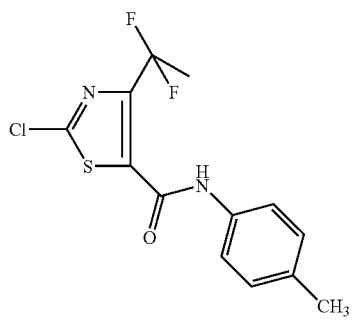

Code Name: 91161
Specs Name: AP-501/40888738
Chemical Name: 2-chloro-N-(4-methylphenyl)-4-(trifluoromethyl)-1,3-thazole-5-carboxamide,

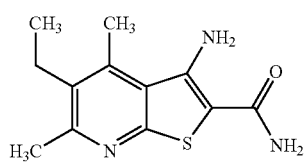

Code Name: 103833
Specs Name: AE-848/34435011
Chemical Name: 3-amino-5-ethyl-4,6-dimethylthieno[2,3-b]pyridine-2-carboxamide,

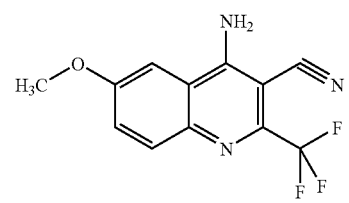

Code Name: 104366
Specs Name: AG-687/25019010
Chemical Name: 4-amino-6-methoxy-2-(trifluoromethyl)-3-quinolinecarbonitrile,

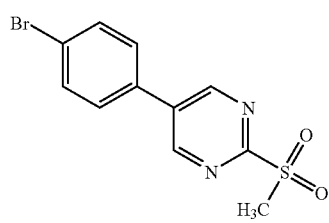

Code Name: 107129
Specs Name: AC-907/25005415
Chemical Name: -(4-bromophenyl)-2-(methylsulfonyl) pyrimidine,

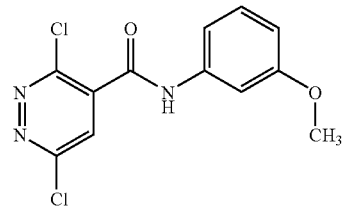

Code Name: 107740
Specs Name: AF-399/40653810
Chemical Name: 3,6-dichloro-N-(3-methoxyphenyl)-4-pyridazinecarboxamide,

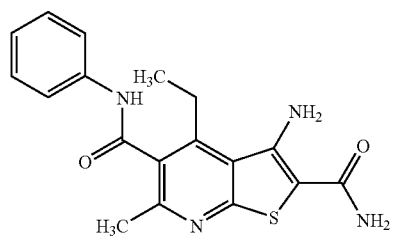

Code Name: 75168
Specs Name: AE-848/34435026
Chemical Name: 3-amino-4-ethyl-6-methyl-N~5~-phenylthieno[2,3-b]pyridine-2,5-dicarboxamide, and

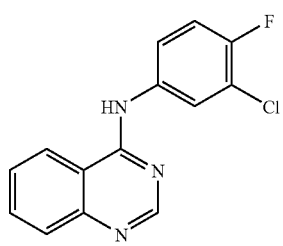

Code Name: 109020
Specs Name: AP-906/416-41102
Chemical Name: N-(3-chloro-4-fluorophenyl)-N-(4-quinazolinyl)amine.

Yet another embodiment of the invention is directed to the compounds of FIGS. 9, 10, 11, 12, 13, 14, and 15, which are analogs of the compounds listed above (see also FIG. 4).

The present invention is also directed to pharmaceutical compositions comprising the HIV inhibitory compounds of the present invention. More particularly, such compounds can be formulated as pharmaceutical compositions using standard pharmaceutically acceptable carriers, fillers, solublizing agents and stabilizers known to those skilled in the art.

The invention is also directed to methods of administering the compounds of the invention to a subject. In one embodiment, the invention provides a method of treating a subject with HIV by administering compounds identified using the methods of the invention description. It is preferred that a compound inhibits HIV replication by at least 10% relative to a control where a compound is not being used to inhibit HIV replication. It is more preferred that a compound of the invention inhibits HIV replication by at least 25% relative to untreated controls. It is further preferred that a compound of the invention inhibits HIV replication by at least 50% relative to untreated controls. It is even further preferred that a compound of the invention inhibits HIV replication by at least 75% relative to untreated controls. It is also preferred that a compound of the invention inhibits HIV replication by at least 90% relative to untreated controls. In yet another aspect, it is preferred that a compound of the invention inhibits HIV replication by at least 95% relative to untreated controls. In one aspect of the invention, HIV replication is inhibited due to inhibition of Rev function or activity. Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating HIV in a subject in need such treatment is provided. The method comprises administering a pharmaceutical composition comprising at least one HIV inhibitory compound of the present invention to a patient in need thereof. Compounds identified by the methods of the invention which inhibit HIV replication can be administered with known anti-HIV compounds or other medications as well.

The invention also encompasses the use pharmaceutical compositions of an appropriate compound, analog, or derivative thereof to practice the methods of the invention, the composition comprising at least one appropriate compound, analog, or derivative thereof and a pharmaceutically-acceptable carrier.

As used herein, the term "pharmaceutically-acceptable carrier" means a chemical composition with which an appropriate compound may be combined and which, following the combination, can be used to administer the appropriate compound to a mammal. Preferably the mammal is a human.

The pharmaceutical compositions useful for practicing the invention may be administered to deliver a dose of between 1 ng/kg/day and 100 mg/kg/day.

Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifingal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

There is clear evidence that Human Immunodeficiency Virus (HIV) is the cause of AIDS and that drugs that inhibit the replication and production of infectious HIV particles are efficacious in the treatment of AIDS (Greene W. C. 2004 Nat. Immunol. 9:867-871). The compounds described in this application are very effective inhibitors of HIV particle formation and are disclosed herein to inhibit HIV Rev function. Without wishing to be bound by any particular theory, these compounds are likely to work by inhibiting one or more of the steps in the Rev pathway described above. They could also inhibit steps downstream of these in the pathway leading to virus particle assembly and release. The compounds are therefore likely to form the chemical basis for new drugs that could be used for the treatment of AIDS.

Development of Cell Lines

The present invention is directed to a safe quantitative in vitro high-throughput assay to screen library compounds for effects on Rev-dependent p24 production. Two cell lines derived from COS cells provide the means of determining whether a library compound has anti-Rev activity-5BD.1 and 2A.22. These cell lines constitutively express HIV-like particles that contain the HIV core proteins as well as HIV envelope protein. The non-infectious virions created by these cells are secreted into the media, where a simple p24 ELISA can quantitatively determine virion production. Production of these virus-like particles is totally dependent on the expression of the Rev protein (for the 5BD.1 cell line), which is also made in these cell lines, or independent of Rev protein expression (the 2A.22 cell line).

The cell line 5BD.1 was created by transfecting COS cells with the wild type HIV-1 structural and regulatory genes gag, gagpol, rev, and env. Each of these genes is necessary but not sufficient for producing infectious HIV virions. Non-infectious virions are produced in 5BD.1 cells via the same pathways as in $CD4^+$ cells. Inhibition of Rev with a library compound would therefore have the same effect on viral production in 5BD.1 cells as in $CD4^+$ cells.

Previous work led to the identification of a small RNA element, named the CTE, from Mason-Pfizer Monkey Virus. When this element is present in the RNA that is expressed from a gene that normally requires Rev co-expression the need for Rev is overcome (U.S. Pat. No. 5,880,276, issued Mar. 9, 1999; U.S. Pat. No. 5,585,263, issued Dec. 17, 1996; Bray et al., (1994) Proc. Natl. Acad. Sci. (USA) 91:1256-1260).

Using the CTE as a component of expression vectors has allowed the creation of a series of expression vectors, which allows expression of HIV proteins in a Rev-independent fashion. The vectors were then used to create stable cell lines that expressed the proteins. One cell line in particular has proved extremely useful. It is called 2A.22 (Srinivasakumar et al. (1997) J. Virol 71:5841-5848). The cell line expressed HIV proteins (Gag-GagPol and Envelope) in a Rev-independent fashion.

The Rev-independence of 2A.22 is useful as a negative control while testing library compounds. When both cell lines 5BD.1 and 2A.22 are grown and tested with the same compound under similar conditions, a reduction in viral production in 5BD.1 and not in 2A.22 indicates a potentially positive score for that compound as a Rev-specific inhibitor. Alternately, if a compound reduced p24 levels in both 5BD.1 and 2A.22, this could indicate a possible harmful interaction with cellular machinery and would rule out that specific compound from further studies.

The non-infectious HIV-like particles created by these cells are secreted into the media, where a simple p24 ELISA can quantitatively determine particle production.

Methods—

Anti-Rev Screening to Identify Compounds

The following steps were performed in a drug screening assay of that led to the identification of the nine parental compounds of the invention described herein. Approximately 40,000 compounds (commercially available from SPECS and BioSPECS, Rijswijk, The Netherlands) were screened in this fashion.

Tissue Culture Assay:
1. 5BD.1 cells were passaged in 2 T225 flasks in medium (IMDM/10% FCS/0.2 mg/ml HygromycinB/1.5 mg/ml G418/0.05 mg/ml gentamycin).

Cells were harvested from 90% confluent flasks with 28.4× $10^6$ cells recovered.
2. 4500 cells per well were plated into columns of tissue culture treated clear 384 well plates in 40 µl per well of medium.
3. The plate was placed into the incubator for one hour.
4. Compounds were diluted from 2 Ξl of 1 mM DMSO stocks in 384 well polypropylene plates by adding 38 µl per well of medium.
5. 10 µl of each diluted compound was transferred to the cell plates.
6. The plates were then incubated overnight for 16 hours.
7. In the morning of the next day the plates were aspirated on a plate washer.
8. 40 µl of fresh medium was added to each well followed by 10 µl of diluted as in step 5.
9. The plates were then incubated for 8 hours and the supernatant was collected for measurement in the p24 ELISA Assay.

p24 ELISA Assay:
10. Dilute primary antibody to 4 µg/ml in DPBS without calcium and magnesium, add 25 µl per well of a 384 well Maxisorp plate, incubate overnight at 4° C.
11. Aspirate coating solution, block for 30-60 minutes with 100 µl ELISA buffer (4 mg/ml BSA, 0.01% Tween20 in DPBS without calcium and magnesium).
12. Wash plates 2×.
13. Add 25 µl of supernatant from step 9 above.
14. Add 10 µl of a 1:250 dilution of biotinylated secondary antibody in 25% lysis buffer/ELISA buffer.
15. Incubate overnight in the refrigerator.
16. Wash plates 3×.
17. The plates were read in a plate reader at 450 nm.

Example 1

Compounds were identified using the primary screening assay that involved the use of a cell line (5BD.1) that was continuously expressing HIV virus-like particles. To measure inhibition, supernatants containing HIV virus-like particles were obtained from the tissue culture assay described above. The amount of HIV particles in the assay was then measured using the ELISA Assay that is also described above. Representative data showing the final ELISA data from the screening of 4,000 of approximately 40,000 compounds screened (commercially available from SPECS and BioSPECS, Rijswijk, The Netherlands) are shown in FIG. 2. 192 compounds were identified in this fashion.

Dose Response Assay in 5BD.1 Cells,

Each of the 192 compounds was then subjected to 3 and 6 point dose response assays in 5BD.1 cells and toxicity testing in the MT-4 T cell line. The dose response assay was performed as follows 3 and 6 Point Dose Response Assays:

Tissue Culture
1. 5BD.1 cells were carried in 2 T175 flasks in medium (IMDM/10% FCS/0.2 mg/ml HygromycinB/1.5 mg/ml G418/0.05 mg/ml gentamycin). Cells were trypsinized and harvested from a 90% confluent flask.
2. 20,000 cells per well were plated into rows A-G of 8 tissue culture treated clear 96-well plates in 135 µl per well of medium without G418 (assay medium). 135 µl of medium only was added to row H.
3. The plates were placed into the incubator for one hour.
4. Compounds were serially diluted 1:3 two times from 1 mM DMSO stocks in DMSO in 96 well polypropylene plates. 8 µl of the DMSO solutions were transferred to another plate and 72 µl of assay medium was added.
5. 15 µl of each diluted compound was transferred to the cell plates in duplicate with the high (10 µM final concentration in rows A-B, 3 µM concentration in rows C-D, 1 µM concentration in rows E-F and DMSO only in rows G-H).
6. The plates were then incubated overnight for 16 hours.
7. In the morning of the next day the medium was removed by hand from all wells.
8. 135 µl of fresh assay medium was added to each well followed by 15 µl of diluted compounds as described in step 5.
9. The plates were then incubated for 24 hours and the medium was harvested.

p24 ELISA Assay:
10. Dilute primary antibody to 4 µg/ml in DPBS without calcium and magnesium, add 50 µl per well of a 96 well Maxisorp plate, incubate overnight at 4° C.
11. Aspirate coating solution, block for 30-60 minutes with 200 µl ELISA buffer (4 mg/ml BSA, 0.01% Tween20 in DPBS without calcium and magnesium).
12. Wash plates 2×.
13. Add 50 µl of the supernatants from step 9 above.
14. Add 15 µl of a 1:750 dilution of biotinylated secondary antibody in 40% lysis buffer/ELISA buffer.
15. Incubate 2 hours at room temperature with shaking.
16. Wash plates 3×.
17. Add 50 µL/well of a 1:10,000 dilution of detection SA-HRP. Incubate at room temperature with shaking for 30 minutes.
18. Wash plates 3×. Add 50 µL/well of TMB substrate solution to all wells and develop for approximately 15 minutes until blue.
19. Stop the reaction with 50 µL/well 0.18M sulfuric acid.
20. Read plate at 450 nm.

Toxicity Assays:

MTS-based toxicity assays were performed in parallel to the 3 and 6 point dose response assays. The assay uses MTS a tetrazolium compound [3-(4,5-dimethylthiazol-2-yl)-5-(3-carboxymethoxyphenyl)-2-(4-sulfophenyl)-2H-tetrazolium, inner salt; MTS(b)] and an electron coupling reagent (phenazine ethosulfate; PES) and was performed according to the directions of its manufacturer Promega, Madison Wis. (see protocol Technical Bulletin #245 from Promega).

Example 2

The six point dose assay in 5BD.1 cells was used to calculate an $IC_{50}$ for the compounds and data from the MT-4 toxicity assay allowed a $TC_{50}$ to be calculated. Data for the eight compounds being claimed in this application is given in Table 1. Representative dose response curves that were used to calculate these data are illustrated for two of the compounds in FIG. 3. The name and chemical structure of the nine compounds are provided in FIG. 4.

TABLE 1

Six point dose response and toxicity assay in 5BD.1 cells and MT4 cells

| Compound Code | $IC_{50}$ (µM) | $TC_{50}$ (µM) | TI ($TC_{50}/IC_{50}$) |
|---|---|---|---|
| 75168 | 3.0 | >100 | >33.3 |
| 89246 | 0.9 | 20 | 22.22 |
| 91161 | 1.9 | 18 | 9.47 |
| 103833 | 0.9 | 32 | 35.6 |
| 104366 | 2.5 | 28 | 11.2 |
| 107129 | 0.25 | 10 | 40.0 |
| 107740 | 4.9 | 50 | 10.2 |
| 109020 | 3.0 | 100 | 33.3 |

Rev Assay

The eight compounds listed in Table 1 were also tested in an assay that measured HIV-1 Rev function. The HIV-1 Rev assay is based upon the use of a reporter for detecting whether drug candidates are capable of inhibiting the function of the viral Rev protein. The reporter used for these assays is the Renilla Luciferase protein, which is an enzyme that produces detectable light when mixed with certain chemicals. For this assay, a cell line has been developed in which the production of the reporter by the cells requires the function of HIV-1 Rev. Therefore, if a drug candidate inhibits the function of Rev, it decreases the amount of the reporter produced by the cells. By using Renilla Luciferase as the reporter, the inhibition of Rev is easily detected as a decrease in the amount of light produced by the cells when mixed with the appropriate chemicals. Furthermore, the cell line for this assay has been engineered to use a second similar reporter (Firefly Luciferase) that detects whether drug candidates are toxic. By using this two reporter, or Dual-Luciferase, approach, compounds that specifically inhibit HIV-1 Rev can be identified. More detailed information about the assay is provided in the table 2 below.

TABLE 2

Details of the HIV-1 Rev Assay

| Parameter | HIV-1 Rev Assay |
|---|---|
| Assay Principal | HIV-1 Rev-dependent Luciferase reporter expression construct engineered into a stable cell line. |
| Reference for Assay Principal | Hope et al. (1990) Proc. Natl. Acad. Sci. USA 87: 7787-7791. |
| Cell Line | HeLa (cervix; epithelial; adenocarcinoma) |
| Genetic Modifications | Stably integrated bicistronic expression construct for both the HIV-1$_{IIIB}$ Rev gene and Firefly Luciferase gene under the control of a single Tet-Off promoter; Stably integrated HIV-1$_{SF2}$ Rev-dependent Renilla Luciferase reporter expression construct for monitoring Rev function. |
| Cell Line Maintenance Media | DMEM supplemented with 10% Tet-Free FBS, L-Glutamine, Pen/Strep, Geneticin (G418), Hygromycin B and Puromycin. |
| Passage | Trypsinized and split 1:5 twice weekly; Fresh cells thawed from LN$_2$ storage routinely to minimize loss of reporter gene expression upon serial passage. |
| Assay Media | DMEM supplemented with 10% Tet-Free FBS, L-Glutamine, Pen/Strep. |
| Standard Assay Conditions | $2 \times 10^4$ cells/well; 96 well format.<br>Drugs tested at 6 concentrations in triplicate assay wells.<br>Cells and drug added to wells in 200 μL total volume.<br>Plates incubated for 24 hours at 37° C. in humidified 5% CO$_2$ atmosphere.<br>Drugs/media removed, cells lysed and assayed for Dual-Luciferase ® reporter expression according to manufacturers kit instructions (Promega, Madison, WI). |
| Endpoint Detection | Firefly Luciferase: luminescence (relative light units) for detection of Tat expression and compound cytotoxicity/non-specificity<br>Renilla Luciferase: luminescence (relative light units) for detection of compound inhibition of Rev function |
| Assay Controls | Doxycycline: turns off Tet-Off promoter to shut down both Firefly and Renilla Luciferase Expression and verify assay system functioning properly<br>Leptomycin B: Positive control; inhibitor of hCRM1 mediated Rev nuclear export.<br>Other positive controls: Currently being identified and tested. |
| Data Analysis | Calculations of compound efficacy for inhibiting Rev function as 50% inhibition of Renilla Luciferase (IC$_{50}$), compound toxicity/non-specificity as 50% inhibition of Firefly Luciferase (TC$_{50}$) and Therapeutic Index (TI = TC$_{50}$/IC$_{50}$). |

Example 3

Compounds were tested in the Rev assay using the maximum high-test concentration possible based on the supplied stocks as shown in Table 3. Compounds were prepared at a 2× high-test concentration by combining drug stock with tissue culture media at a ratio of 5 μL of drug to 995 μL of media. This 2× high-test sample was subsequently serially diluted in tissue culture media using 1/2 log dilutions. This series of 2× concentrated drug was subsequently diluted 1:1 by combining with an equal volume of cells in media in the 96-well plates used for the assay. The results of the assay for all eight compounds are shown in Table 4. Representative data for two of the compounds is also depicted in FIG. 5.

TABLE 3

Compound Information

| Compound | Stock Concentration Provided (mM) | High-Test Concentration Used (μM) |
|---|---|---|
| 75168 | 10.7 | 26.75 |
| 89246 | 21.8 | 54.5 |
| 91161 | 15.8 | 39.5 |
| 103833 | 15.04 | 37.6 |
| 104366 | 31.8 | 79.5 |
| 107129 | 21.2 | 53.0 |
| 107740 | 11.7 | 29.25 |
| 109020 | 16.3 | 40.75 |

TABLE 4

Rev Assay Results for Compounds

| Compound Code | IC$_{50}$ (μM) | TC$_{50}$ (μM) | TI (TC$_{50}$/IC$_{50}$) |
|---|---|---|---|
| 75168 | 2.42 | 7.91 | 3.27 |
| 89246 | 0.48 | 8.41 | 17.52 |
| 91161 | 9.73 | >39.5 | >4.06 |
| 103833 | 1.07 | >37.6 | >35.14 |
| 104366 | 2.24 | 17.2 | 7.68 |
| 107129 | 7.48 | 30.9 | 4.13 |
| 107740 | 8.00 | 18.5 | 2.31 |
| 109020 | 8.98 | >40.8 | >4.54 |
| Leptomycin B | 0.00822 | 0.0200 | 2.43 |
| Leptomycin B | 0.00817 | 0.0192 | 2.35 |

It should be noted that "Toxicity" in this assay reflects non-specific compound activity in the assay as demonstrated by a reduction in the Firefly Luciferase signal, which is Rev-independent. This does not necessarily correlate with cell killing. Leptomycin B is a control compound known to inhibit Rev function.

Anti-HIV Efficacy Evaluation in Fresh Human Peripheral Blood Mononuclear Cells (PBMCs)

Compounds were evaluated for their ability to inhibit HIV replication in fresh human PBMCs. The assay was performed as follows.

Preparation of PBMCs

Fresh human PBMCs, seronegative for HIV and HBV, were isolated from screened donors (Interstate Blood Bank, Inc. Memphis, Tenn.). Cells were pelleted/washed 2-3 times by low speed centrifugation and re-suspension in PBS to remove contaminating platelets. The Leukophoresed blood was then diluted 1:1 with Dulbecco's Phosphate Buffered Saline (DPBS) and layered over 14 mL of Lymphocyte Separation Medium (LSM; Cellgro® by Mediatech, Inc.; density 1.078+/−0.002 g/ml; Cat.#85-072-CL) in a 50 mL centrifuge tube and then centrifuged for 30 minutes at 600×g. Banded PBMCs were gently aspirated from the resulting interface and subsequently washed 2× with PBS by low speed centrifugation. After the final wash, cells were enumerated by trypan blue exclusion and re-suspended at $1 \times 10^7$ cells/mL in RPMI 1640 supplemented with 15% Fetal Bovine Serum (FBS), and 2 mM L-glutamine, 4 μg/mL Phytohemagglutinin (PHA-P, Sigma). The cells were allowed to incubate for 48-72 hours at 37° C. After incubation, PBMCs were centrifuged and resuspended in RPMI 1640 with 15% FBS, 2 mM L-glutamine, 100 U/mL penicillin, 100 μg/mL streptomycin, 10 μg/mL gentamycin, and 20 U/mL recombinant human IL-2 (R&D Systems, Inc). IL-2 is included in the culture medium to maintain the cell division initiated by the PHA mitogenic stimulation. PBMCs were maintained in this medium at a concentration of $1$-$2 \times 10^6$ cells/mL with biweekly medium changes until used in the assay protocol. Cells were kept in culture for a maximum of two weeks before being deemed too old for use in assays and discarded. Monocytes were depleted from the culture as the result of adherence to the tissue culture flask.

Viral Assay

For the standard PBMC assay, PHA-P stimulated cells from at least two normal donors were pooled (mixed together), diluted in fresh medium to a final concentration of $1 \times 10^6$ cells/mL, and plated in the interior wells of a 96 well round bottom microplate at 50 μL/well ($5 \times 10^4$ cells/well) in a standard format developed by the Infectious Disease Research department of Southern Research Institute. Pooling (mixing) of mononuclear cells from more than one donor is used to minimize the variability observed between individual donors, which results from quantitative and qualitative differences in HIV infection and overall response to the PHA and IL-2 of primary lymphocyte populations. Each plate contains virus/cell control wells (cells plus virus), experimental wells (drug plus cells plus virus) and compound control wells (drug plus media without cells, necessary for MTS monitoring of cytotoxicity). Since HIV-1 is not cytopathic to PBMCs, this allows the use of the same assay plate for both antiviral activity and cytotoxicity measurements. Test drug dilutions were prepared at a 2× concentration in microtiter tubes and 100 μL of each concentration was placed in appropriate wells using the standard format. 50 μL of a predetermined dilution of virus stock was placed in each test well (final MOI≅0.1). The PBMC cultures were maintained for seven days following infection at 37° C., 5% $CO_2$. After this period, cell-free supernatant samples were collected for analysis of reverse transcriptase activity as a measure of virus release. Following removal of supernatant samples, compound cytotoxicity was measured by addition of MTS to the plates for determination of cell viability. Wells were also examined microscopically and any abnormalities were noted.

Reverse Transcriptase Activity Assay

A microtiter plate-based reverse transcriptase (RT) reaction was utilized (Buckheit et al., AIDS Research and Human Retroviruses 7:295-302, 1991). Tritiated thymidine triphosphate (3H-TTP, 80 Ci/mmol, NEN) was received in 1:1 $dH_2O$:Ethanol at 1 mCi/mL. Poly rA:oligo dT template:primer (Pharmacia) was prepared as a stock solution by combining 150 μL poly rA (20 mg/mL) with 0.5 mL oligo dT (20 units/mL) and 5.35 mL sterile $dH_2O$ followed by aliquoting (1.0 mL) and storage at −20° C. The RT reaction buffer was prepared fresh on a daily basis and consisted of 125 μL 1.0 M EGTA, 125 μL $dH_2O$, 125 μL 20% Triton X100, 50 μL 1.0 M Tris (pH 7.4), 50 μL 1.0 M DTT, and 40 μL 1.0 M $MgCl_2$. The final reaction mixture was prepared by combining 1 part $^3$H-TTP, 4 parts $dH_2O$, 2.5 parts poly rA:oligo dT stock and 2.5 parts reaction buffer. Ten microliters of this reaction mixture was placed in a round bottom microtiter plate and 15 μL of virus containing supernatant was added and mixed. The plate was incubated at 37° C. for 60 minutes. Following incubation, the reaction volume was spotted onto DE81 filtermats (Wallac), washed 5 times for 5 minutes each in a 5% sodium phosphate buffer or 2×SSC (Life Technologies). Next, they were washed 2 times for 1 minute each in distilled water, 2 times for 1 minute each in 70% ethanol, and then dried. Incorporated radioactivity (counts per minute, CPM) was quantified using standard liquid scintillation techniques.

MTS Staining for PBMC Viability to Measure Cytotoxicity

At assay termination, assay plates were stained with the soluble tetrazolium-based dye MTS (CellTiter 96 Reagent, Promega) to determine cell viability and quantify compound toxicity. The mitochondrial enzymes of metabolically active cells metabolize MTS to yield a soluble formazan product. This allows the rapid quantitative analysis of cell viability and compound cytotoxicity. The MTS is a stable solution that does not require preparation before use. At termination of the assay, 20 μL of MTS reagent was added per well. The microtiter plates were then incubated 4-6 hrs at 37° C. The incubation intervals were chosen based on empirically determined times for optimal dye reduction. Adhesive plate sealers were used in place of the lids, the sealed plate was inverted several times to mix the soluble formazan product and the plate was read spectrophotometrically at 490/650 nm with a Molecular Devices Vmax or SpectraMaxPlus plate reader.

Virus Information

The HIV-1 clinical isolate BR/93/021 was obtained from the NIH AIDS Research and Reference Reagent Program. This virus was originally isolated from a seropositive individual in Brazil and has been characterized as an Envelope Subtype B and as an R5-tropic isolate. The HIV-1 molecular clone NL4-3 was obtained from the NIH AIDS Research and Reference Reagent Program. Virus stocks were prepared by transfection of plasmid DNA into cells using standard techniques. A Pre-titered aliquot of each virus was removed from the freezer ($LN_2$) and thawed rapidly to room temperature in a biological safety cabinet immediately before use.

Example 4

Compounds were tested in the PBMC assay using the maximum high-test concentration possible based on the supplied stocks which are listed in table 3. Compounds were prepared at a 2× high-test concentration by combining drug stock with tissue culture media at a ratio of 5 μL of drug to 995 μL of media. This 2× high-test sample was subsequently serially diluted in tissue culture media using 1/2 log dilutions. This series of 2× concentrated drug was subsequently diluted 1:1 by combining with an equal volume of cells in media in the 96-well plates used for the assay. The results of the assay for all eight compounds are shown in Table 5. Representative data for two of the compounds with each virus are shown in FIGS. 6 and 7.

TABLE 5

Results for Compounds Against HIV-1 in Fresh Human PBMCs

| Compound | HIV-1 BR/93/021 | | | HIV-1 NL4-3 | | |
|---|---|---|---|---|---|---|
| | $IC_{50}$ (μM) | $TC_{50}$ (μM) | TI ($TC_{50}$/$IC_{50}$) | $IC_{50}$ (μM) | $TC_{50}$ (μM) | TI ($TC_{50}$/$IC_{50}$) |
| 75168 | 2.14 | >26.8 | >12.52 | 16.9 | >26.8 | >1.59 |
| 89246 | 0.47 | 32.7 | 69.57 | 1.47 | 21.9 | 14.90 |
| 91161 | 1.94 | 23.3 | 12.01 | 2.28 | 13.5 | 5.92 |
| 103833 | 0.29 | >37.6 | >129.66 | 2.22 | >37.6 | >16.94 |
| 104366 | 0.64 | 24.9 | 38.91 | 0.92 | 22.0 | 23.91 |
| 107129 | 1.80 | 6.26 | 3.48 | 2.12 | 4.13 | 1.95 |
| 107740 | 0.20 | 18.8 | 94.00 | 1.61 | 14.4 | 8.94 |
| 109020 | 13.2 | >40.8 | >3.09 | 26.4 | >40.8 | >1.55 |
| AZT | 0.00247 | >1.0 | >404.86 | 0.00062 | >1.0 | >1612.90 |

AZT was used as an anti-viral control.

Efficacy Evaluation in U1 Cells Latently Infected with HIV-1

U1 Cell Culture

U1 cells were obtained from the AIDS Research and Reference Reagent Program and maintained under standard culture conditions in RPMI 1640 supplemented with 10% fetal bovine serum (heat inactivated), 2 mM L-glutamine, 100 U/mL penicillin and 100 μg/mL streptomycin. U1 cells are derived from the histocytic leukemia cell line U937, and contain an integrated copy of a cytokine and/or phorbol inducible provirus (HIV-1$_{IIIB}$). Cultures were maintained in such a way as to ensure exponential growth of the populations. Addition of TNF-α to the cell culture induces HIV-1, so that inhibition of virus production indicates an inhibition of a post-integration function of the HIV-1 life cycle. This is where an inhibitor of Rev function would be expected to act. Cells were collected by centrifugation and counted by hemacytometer Assay Setup At the time of the assay, cells were collected by centrifugation and counted by hemacytometer. If cell viability by Trypan Blue dye exclusion was less than 70% the assay was terminated. The cells were adjusted to 5×10$^4$ cells/mL and 100 μL placed in 96 well plates with 100 μL media containing a final concentration of 5 ng/mL TNF-α and the test compound. Cultures were incubated for 3 days and supernatants harvested. Compound toxicity was determined by MTS dye reduction. Virus expression was measured by supernatant reverse transcriptase activity.

Reverse Transcriptase Activity Assay

Reverse transcriptase was assayed to measure virus particle release as described above for the PBMC assay.

MTS Staining for Cell Viability

At assay termination, the assay plates were stained with the soluble tetrazolium-based dye MTS (CellTiter 96 Reagent, Promega) to determine cell viability and quantify compound toxicity as described for the PBMC assay.

Example 5

Compounds were tested in the U1 latency assay using the maximum high-test concentration possible based on the supplied stocks which are listed in table 3. Compounds were tested using the maximum high-test concentration possible based on the supplied stocks. Compounds were prepared at a 2× high-test concentration by combining drug stock with tissue culture media at a ratio of 5 μL of drug to 995 μL of media. This 2× high-test sample was subsequently serially diluted in tissue culture media using 1/2 log dilutions. This series of 2× concentrated drug was subsequently diluted 1:1 by combining with an equal volume of cells in media in the 96-well plates used for the assay. Temacrazine a known inhibitor of HIV transcription was used as a control compound that is active in the post-integration part of the HIV life cycle.

The results of the assay for seven of the eight compounds are shown in Table 6. Representative data for two of the compounds and the control are shown in FIG. 8.

TABLE 6

Results for Compounds in U1 Cell Assay

| Compound | $IC_{50}$ (μM) | $TC_{50}$ (μM) | TI ($TC_{50}$/$IC_{50}$) |
|---|---|---|---|
| 89246 | 0.24 | 24.6 | 102 |
| 91161 | 16.5 | 22.3 | 1.35 |
| 103833 | 0.40 | >37.6 | >94 |
| 104366 | <0.25 | 12.4 | >49.6 |
| 107129 | >53.0 | >53.0 | N/A |
| 107740 | 1.1 | >29.3 | >26.6 |
| 109020 | 0.27 | >40.8 | >151 |
| Temacrazine | 0.002 | >0.5 | >250 |

Analogs of the Parental Compounds

Analog searches of 7 of the parental compounds were performed on the Specs database of compounds using ISIS software from MDL Information Systems Inc. (Elsevier MDL, 14600 Catalina Street San Leandro, Calif. 94577). Analogs of each of the seven compounds were found and are shown in FIGS. 9-15. The following number of analogs were found for each compound.

TABLE 7

Analogs for each compound

| Compound | Number of analogs |
|---|---|
| 89246 | 4 |
| 91161 | 13 |
| 103833 | 29 |
| 104366 | 6 |
| 107129 | 7 |
| 107740 | 6 |
| 109020 | 18 |

Compounds were tested using the maximum high-test concentration possible based on the supplied stocks. Compounds were prepared at a 2× high-test concentration by combining drug stock with tissue culture media at a ratio of 5 μL of drug to 995 μL of media. This 2× high-test (HT) sample was subsequently serially diluted in tissue culture media using 1/2 log dilutions. This series of 2× concentrated drug was subsequently diluted 1:1 by combining with an equal volume of cells in media in the 96-well plates used for the assay. The results are shown in Table 8.

TABLE 8

Results for Analogs in U1 Cell Assay

| Compound | HT Conc. | $IC_{50}$ | $TC_{50}$ | TI |
|---|---|---|---|---|
| 89246 | 54.5 μM | <0.172 μM | 29.0 μM | >169 |
| 111 | 50.0 μM | 1.70 μM | >50.0 μM | >29.4 |
| 112 | 50.0 μM | 1.08 μM | >50.0 μM | >46.3 |
| 113 | 75.0 μM | 27.4 μM | >75.0 μM | >2.74 |
| 114 | 75.0 μM | 14.4 μM | >75.0 μM | >5.21 |
| 104366 | | | | |
| 211 | 75 μM | 9.11 μM | 48.5 μM | 5.32 |
| 212 | 50 μM | 0.484 μM | 28.6 μM | 59.1 |
| 213 | 75 μM | 0.826 μM | 58.6 μM | 70.9 |
| 214 | 75 μM | 9.19 μM | >75.0 μM | >8.16 |
| 215 | 37.5 μM | 32.2 μM | >37.5 μM | >1.16 |
| 216 | 75 μM | 2.73 μM | 13.0 μM | 4.76 |
| 103833 | | | | |
| 311 | 75 μM | 1.65 μM | >75.0 μM | >45.5 |
| 312 | 75 μM | 7.13 μM | >75.0 μM | >10.5 |
| 313 | 50 μM | >50.0 μM | >50.0 μM | N/A |
| 314 | 75 μM | 2.11 μM | >75.0 μM | >35.5 |
| 315 | 75 μM | 0.750 μM | >75.0 μM | >100 |
| 316 | 75 μM | 23.4 μM | >75.0 μM | >3.21 |
| 317 | 75 μM | >75.0 μM | >75.0 μM | N/A |
| 318 | 75 μM | <0.237 μM | >75.0 μM | >316 |
| 319 | 37.5 μM | 20.2 μM | >37.5 μM | >1.86 |
| 320 | 75 μM | 0.522 μM | >75.0 μM | >144 |
| 321 | 75 μM | 1.94 μM | >75.0 μM | >38.7 |
| 322 | 75 μM | 8.84 μM | 17.4 μM | 1.97 |
| 323 | 75 μM | 0.745 μM | 22.6 μM | 30.3 |
| 324 | 75 μM | 2.19 μM | >75.0 μM | >34.2 |
| 325 | 75 μM | 0.281 μM | >75.0 μM | >267 |
| 326 | 75 μM | <0.237 μM | 52.8 μM | >223 |
| 327 | 75 μM | 0.601 μM | 65.8 μM | 109 |
| 328 | 75 μM | 1.06 μM | 37.0 μM | 34.9 |
| 329 | 75 μM | 2.03 μM | 58.4 μM | 28.8 |
| 330 | 75 μM | 6.91 μM | >75.0 μM | >10.9 |
| 331 | 75 μM | 66.0 μM | >75.0 μM | >1.14 |
| 332 | 75 μM | >75.0 μM | 22.5 μM | <0.30 |
| 333 | 20 μM | >20.0 μM | >20.0 μM | N/A |
| 334 | 75 μM | 2.37 μM | >75.0 μM | >31.6 |
| 335 | 75 μM | 1.41 μM | 53.9 μM | 38.2 |
| 336 | 75 μM | 2.92 μM | >75.0 μM | >25.7 |
| 337 | 75 μM | 2.40 μM | >75.0 μM | >31.3 |
| 338 | 75 μM | 5.23 μM | >75.0 μM | >14.3 |
| 339 | 75 μM | 1.28 μM | 38.3 μM | 29.9 |
| 91161 | | | | |
| 411 | 75 μM | >75.0 μM | >75.0 μM | N/A |
| 412 | 75 μM | 16.7 μM | 51.7 μM | 3.10 |
| 413 | 75 μM | 20.7 μM | 50.7 μM | 2.45 |
| 414 | 75 μM | 14.5 μM | 14.7 μM | 1.01 |
| 415 | 75 μM | 37.3 μM | 51.2 μM | 1.37 |
| 416 | 75 μM | 0.767 μM | >75.0 μM | >97.8 |
| 417 | 75 μM | 1.62 μM | 51.9 μM | 32.0 |
| 418 | 75 μM | 2.18 μM | >75.0 μM | >34.4 |
| 419 | 75 μM | 1.86 μM | 49.4 μM | 26.6 |
| 420 | 75 μM | 6.80 μM | >75.0 μM | >11.0 |
| 421 | 75 μM | >75.0 μM | >75.0 μM | N/A |
| 422 | 75 μM | 14.3 μM | >75.0 μM | >5.24 |
| 423 | 75 μM | 42.4 μM | >75.0 μM | >1.77 |
| 107740 | | | | |
| 511 | 75 μM | 14.3 μM | 17.3 μM | 1.21 |
| 512 | 75 μM | 26.3 μM | >75.0 μM | >2.85 |
| 513 | 75 μM | 7.05 μM | >75.0 μM | >10.6 |
| 514 | 75 μM | >75.0 μM | >75.0 μM | N/A |
| 515 | 75 μM | 13.6 μM | >75.0 μM | >5.51 |
| 516 | 6.25 μM | >6.25 μM | >6.25 μM | N/A |
| 107129 | | | | |
| 611 | 75 μM | 17.5 μM | 15.0 μM | 0.86 |
| 612 | 75 μM | >75.0 μM | >75.0 μM | N/A |
| 613 | 75 μM | >75.0 μM | >75.0 μM | N/A |
| 614 | 75 μM | >75.0 μM | >75.0 μM | N/A |
| 615 | 75 μM | 11.9 μM | >75.0 μM | >6.30 |
| 616 | 75 μM | 0.915 μM | >75.0 μM | >82.0 |
| 617 | 75 μM | >75.0 μM | >75.0 μM | N/A |
| 618 | 75 μM | 18.3 μM | 53.6 μM | 2.93 |
| 109020 | | | | |
| 718 | 75 μM | 47.2 μM | 50.1 μM | 1.06 |
| 719 | 75 μM | 1.73 μM | >75.0 μM | >43.4 |
| 720 | 75 μM | 3.66 μM | >75.0 μM | >20.5 |
| 722 | 75 μM | 21.9 μM | 35.0 μM | 1.60 |
| 728 | 75 μM | 13.4 μM | 17.5 μM | 1.31 |
| 729 | 75 μM | >75.0 μM | >75.0 μM | N/A |
| 730 | 75 μM | >75.0 μM | >75.0 μM | N/A |
| 731 | 75 μM | 1.65 μM | >75.0 μM | >45.5 |
| 734 | 12.5 μM | 4.07 μM | >12.5 μM | >3.07 |
| 748 | 75 μM | 10.5 μM | 33.0 μM | 3.14 |
| 749 | 75 μM | 2.05 μM | 19.5 μM | 9.51 |
| 750 | 75 μM | >75.0 μM | >75.0 μM | N/A |
| 751 | 75 μM | 71.4 μM | >75.0 μM | >1.05 |
| 752 | 75 μM | >75.0 μM | >75.0 μM | N/A |
| 753 | 75 μM | 47.1 μM | 48.0 μM | 1.02 |
| 754 | 75 μM | 3.69 μM | 15.1 μM | 4.09 |
| 755 | 75 μM | 1.78 μM | >75.0 μM | >42.1 |
| 756 | 75 μM | 1.74 μM | 52.0 μM | 29.9 |
| Temacrazine | 500 nM | 1.56 nM | >500 nM | >320 |
| Temacrazine | 500 nM | 3.84 nM | >500 nM | >130 |

The disclosures of each and every patent, patent application, and publication cited herein are hereby incorporated by reference herein in their entirety.

One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

What is claimed is:

1. A method of inhibiting HIV replication, said method comprising contacting a cell comprising HIV with an effective amount of compound 103833:

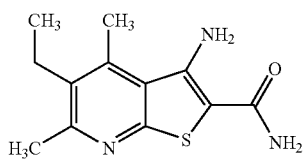
3-amino-5-ethyl-4,6-dimethylthieno[2,3-b]pyridine-2-carboxamide.
2. The method of claim 1, wherein said compound inhibits REV function.
3. The method of claim 1, wherein HIV virion production is dependent on Rev protein expression.
* * * * *